US007081461B1

(12) United States Patent  
Mortlock et al.

(10) Patent No.: US 7,081,461 B1  
(45) Date of Patent: Jul. 25, 2006

(54) QUINAZOLINE COMPOUNDS AND PHARMACEUTICAL COMPOSITIONS CONTAINING THEM

(75) Inventors: Andrew Austen Mortlock, Macclesfield (GB); Nicholas John Keen, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 327 days.

(21) Appl. No.: 10/088,854

(22) PCT Filed: Sep. 18, 2000

(86) PCT No.: PCT/GB00/03556

§ 371 (c)(1),  
(2), (4) Date: Mar. 21, 2002

(87) PCT Pub. No.: WO01/21594

PCT Pub. Date: Mar. 29, 2001

(30) Foreign Application Priority Data

Sep. 21, 1999 (GB) ................... 9922152.5  
Sep. 21, 1999 (GB) ................... 9922156.6  
Sep. 21, 1999 (GB) ................... 9922159.0

(51) Int. Cl.  
*A61K 31/517* (2006.01)  
*A61K 31/535* (2006.01)  
*A01N 43/54* (2006.01)  
*C07D 413/00* (2006.01)  
*C07D 239/72* (2006.01)  
*A61P 35/00* (2006.01)  
*C07C 211/00* (2006.01)

(52) U.S. Cl. .................. 514/266.31; 514/266.3; 514/266.4; 514/234.5; 544/116; 544/287; 544/293

(58) Field of Classification Search ............ 514/266.2, 514/266.21, 266.23, 266.4, 231.5, 227.8, 514/228.2, 233.8, 266.3, 266.31, 234.5; 544/60, 544/61, 116, 284, 293, 287  
See application file for complete search history.

(56) References Cited

U.S. PATENT DOCUMENTS 5,616,582 A * 4/1997 Barker ................... 514/234.5  
6,184,225 B1 * 2/2001 Thomas et al. ......... 514/234.5  
6,291,455 B1 * 9/2001 Thomas et al. ......... 514/231.5

FOREIGN PATENT DOCUMENTS

| EP | 566226 | 10/1993 |
|---|---|---|
| WO | WO 9220642 | 11/1992 |
| WO | WO 9609294 | 3/1996 |
| WO | WO 9615118 | 5/1996 |
| WO | WO 9630347 | 10/1996 |
| WO | WO 9722596 | 6/1997 |
| WO | WO 9730034 | 8/1997 |
| WO | WO 9730035 | 8/1997 |
| WO | WO 9732856 | 9/1997 |
| WO | WO 9961428 | 12/1999 |

OTHER PUBLICATIONS

Bischoff et. al., "A homologue of *Drosophila* aurora kinase . . . ", The EMBO Journal, 1998, vol. 17, No. 11, pp. 3052-3065.*  
March, J. "Advanced Organic Chemistry Reactions, Mechanisms, and Structure" 4th Edition, (c) 1992, John Wiley & Sons, Inc., New York, NY., p. 527.*  
Kubo, K. et al.: "A Novel Series of 4-Phenoxy-Quinolines:" *Bioorganic & Medicinal Chemistry Letters*, vol. 7, No. 23, 1997, pp. 2935-2940, XP000960788 Oxford; p. 2935-p. 2939.  
Rama Krishna Narla et al.: "4-(3'-bromo-4'-hydroxyphenyl)-amino-6, 7-D Imethoxyquinazoline:" *Clinical Cancer Research*, vol. 4, No. 6, 1998, pp. 1405-1414, XP002113201 The American Association for Cancer Research, US; ISSN: 1078-0432; p. 1405-p. 1408.

* cited by examiner

*Primary Examiner*—James O. Wilson  
*Assistant Examiner*—Tamthom N. Truong  
(74) *Attorney, Agent, or Firm*—Lucy Padget

(57) ABSTRACT

The use of a compound of formula (I)

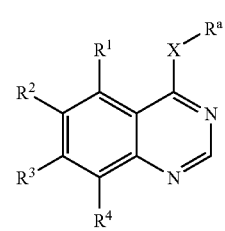

(I)

or a salt, ester or amide thereof;  
where X is O, or S, S(O) or $S(O)_2$, NH or $NR^8$ where $R^8$ is hydrogen or $C_{1-6}$alkyl;  
$R^a$ is a 3-quinoline group or a group of sub-formula (i)

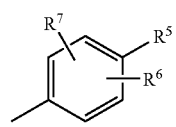

(i)

where $R^5$, $R^6$ and $R^7$ are various specific organic groups, in the preparation of a medicament for use in the inhibtion of aurora 2 kinase.

Novel compounds of formula (I) and pharmaceutical compositions useful in the treatment of cancer are also described and claimed.

8 Claims, No Drawings

QUINAZOLINE COMPOUNDS AND PHARMACEUTICAL COMPOSITIONS CONTAINING THEM

This application is a US National Stage under 35 U.S.C § 371 of International Application No. PCT/GB00/03556 (filed 18 Sep. 2000) which claims priority under 35 U.S.C. § 119(a)–(d) to Application No. GB 9922156.6 filed on 21 Sep. 1999, GB 9922152.5 filed on 21 Sep. 1999 and GB 9922159.0 filed on 21 Sep. 1999.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle For example, the CDK4 protein appears to control entry into the cell cycle (the G0-G 1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672–1677; Pines, 1995, Seminars in Cancer Biology 6: 63–72). Other studies (Loda et al., 1997, Nature Medicine 3(2): 231–234; Gemma et al., 1996, International Journal of Cancer 68(5): 605–11; Elledge et al. 1996, Trends in Cell Biology 6; 388–392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ipl1 proteins. *Drosophila* aurora and *S. cerevisiae* Ipl1, which are highly homologous at the amino acid sequence level, encode serine/threonine protein kinases. Both aurora and Ipl1 are known to be involved in controlling the transition from the G2 phase of the cell cycle through mitosis, centrosome function, formation of a mitotic spindle and proper chromosome separation/segregation into daughter cells. The two human homologues of these genes, termed aurora1 and aurora2, encode cell cycle regulated protein kinases. These show a peak of expression and kinase activity at the G2/M boundary (aurora2) and in mitosis itself (aurora1). Several observations implicate the involvement of human aurora proteins, and particularly aurora2 in cancer. The aurora2 gene maps to chromosome 20q13, a region that is frequently amplified in human tumours including both breast and colon tumours. Aurora2 may be the major target gene of this amplicon, since aurora2 DNA is amplified and aurora2 mRNA overexpressed in greater than 50% of primary human colorectal cancers. In these tumours aurora2 protein levels appear greatly elevated compared to adjacent normal tissue. In addition, transfection of rodent fibroblasts with human aurora2 leads to transformation, conferring the ability to grow in soft agar and form tumours in nude mice (Bischoff et al., 1998, The EMBO Journal. 17(11): 3052–3065). Other work (Zhou et al., 1998, Nature Genetics. 20(2): 189–93) has shown that artificial overexpression of aurora2 leads to an increase in centrosome number and an increase in aneuploidy.

Importantly, it has also been demonstrated that abrogation of aurora2 expression and function by antisense oligonucleotide treatment of human tumour cell lines (WO 97/22702 and WO 99/37788) leads to cell cycle arrest in the G2 phase of the cell cycle and exerts an antiproliferative effect in these tumour cell lines. This indicates that inhibition of the function of aurora2 will have an antiproliferative effect that may be useful in the treatment of human tumours and other hyperproliferative diseases.

A number of quinazoline derivatives have been proposed hitherto for use in the inhibition of various kinases. For example, WO 96/09294, WO 96/15118 and WO 99/06378 describe the use of certain quinazoline compounds as receptor tyrosine kinase inhibitors, which may be useful in the treatment of proliferative disease.

The applicants have found a series of compounds which inhibit the effect of the aurora2 kinase and which are thus of use in the treatment of proliferative disease such as cancer, in particular in such diseases such as colorectal or breast where aurora 2 kinase is known to be active.

The present invention provides the use of a compound of formula (I)

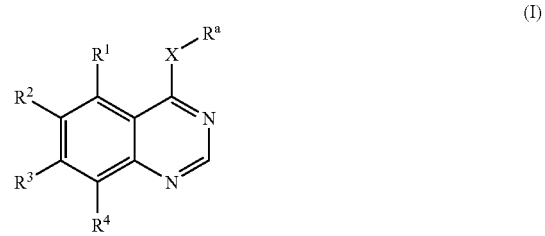

or a salt, ester, amide or prodrug thereof;

where X is O, or S, S(O) or S(O)$_2$, NH or NR$^8$ where R$^8$ is hydrogen or C$_{1-6}$alkyl;

R$^a$ is a 3-quinoline group or a group of sub-formula (i)

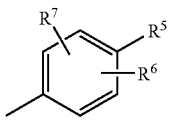

where $R^5$ is either a group —Z—$(CH_2)_n$—$R^9$, halogen, a group of formula $NR^{10}R^{10'}$, an optionally subsitituted hydrocarbyl group (other than ethenyl substituted by a carboxy group or an amide or sulphonamide derivative thereof), an optionally substituted heterocyclyl group or an optionally substituted alkoxy group; where Z is O or S, n is 0, or an integer of from 1 to 6, $R^9$ is hydrogen or optionally substituted hydrocarbyl or optionally substituted heterocyclyl; $R^{10}$ and $R^{10'}$ are independently selected from hydrogen, optionally substituted hydrocarbyl or optionally substituted heterocyclyl, or $R^{10}$ and $R^{10'}$ together with the nitrogen atom to which they are attached form an optionally substituted heterocyclic ring which may optionally contain further heteroatoms, or an azo group of formula —N═N—$R^{11}$ where $R^{11}$ is an optionally substituted hydrocarbyl group or optionally substituted heterocycyl group;

$R^6$ and $R^7$ are independently selected from hydrogen, halo, $C_{1-4}$alkyl, $C_{1-4}$ alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and $R^1$, $R^2$, $R^3$, $R^4$ are independently selected from halogeno, cyano, nitro, $C_{1-3}$alkylsulphanyl, —N(OH)$R^{12}$ (wherein $R^{12}$ is hydrogen, or $C_{1-3}$alkyl), or $R^{14}X^1$— (wherein $X^1$ represents a direct bond, —O—, —$CH_2$—, —OC(O)—, —C(O)—, —S—, —SO—, —$SO_2$—, —$NR^{15}$C(O)—, —C(O)$NR^{16}$—, —$SO_2NR^{17}$—, —$NR^{18}SO_2$— or —$NR^{19}$— (wherein $R^{15}$, $R^{16}$, $R^{17}$, $R^{18}$ and $R^{19}$ each independently represents hydrogen, $C_{1-3}$alkyl or $C_{1-3}$alkoxy$C_{2-3}$alkyl), and $R^{14}$ is hydrogen, optionally substituted hydrocarbyl, optionally substituted heterocyclyl or optionally substituted alkoxy); in the preparation of a medicament for use in the inhibition of aurora 2 kinase.

In particular, such medicaments are useful in the treatment of proliferative disease such as cancer, and in particular cancers where aurora 2 is upregulated such as colon or breast cancers.

In this specification the term 'alkyl' when used either alone or as a suffix includes straight chained or branched structures. Unless otherwise stated, these groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocyclic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynyl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term "functional group" refers to reactive substituents such as nitro, cyano, halo, oxo, ═$CR^{78}R^{79}$, C(O)$_xR^{77}$, O$R^{77}$, S(O)$_yR^{77}$, $NR^{78}R^{79}$, C(O)$NR^{78}R^{79}$, OC(O)$NR^{78}R^{79}$, ═NO$R^{77}$, —$NR^{77}$C(O)$_xR^{78}$, —$NR^{77}$CON$R^{78}R^{79}$, —N═C$R^{78}R^{79}$, S(O)$_yNR^{78}R^{79}$ or —$NR^{77}$S(O)$_yR^{78}$ where $R^{77}$, $R^{78}$ and $R^{79}$ are independently selected from hydrogen, optionally substituted hydrocarbyl, optionally substituted heterocyclyl or optionally substituted alkoxy, or $R^{78}$ and $R^{79}$ together form an optionally substituted ring which optionally contains further heteroatoms such as oxygen, nitrogen, S, S(O) or S(O)$_2$, where x is an integer of 1 or 2, y is 0 or an integer of 1–3.

Suitable optional substituents for hydrocarbyl, heterocyclyl or alkoxy groups $R^{77}$, $R^{78}$ and $R^{79}$ as well as rings formed by $R^{78}$ and $R^{79}$ include halo, perhaloalkyl such as trifluoromethyl, mercapto, thioalkyl, hydroxy, carboxy, alkoxy, heteroaryl, heteroaryloxy, cycloalkyl, cycloalkenyl, cycloalkynyl, alkenyloxy, alkynyloxy, alkoxyalkoxy, aryloxy (where the aryl group may be substituted by halo, nitro, or hydroxy), cyano, nitro, amino, mono- or di-alkyl amino, oximino or S(O)$_yR^{90}$ where y is as defined above and $R^{90}$ is a hydrocarbyl group such as alkyl.

Certain compounds of formula (I) may include a chiral centre and the invention includes the use of all enantiomeric forms thereof, as well as mixtures thereof including racemic mixtures.

In a particular embodiment, in the compounds of formula (I), at least one of $R^1$, $R^2$, $R^3$ and $R^4$ is a group $R^{14}X^1$— where $X^1$ is as defined in relation to formula (I) and $R^{14}$ is hydrogen or an alkyl group, optionally substituted with one or more groups selected from functional groups as defined above, or alkenyl, alkynyl, aryl, heterocyclyl, cycloalkyl, cycloalkenyl or cycloalkynyl, any of which may be substituted with a functional group as defined above, and where any aryl, heterocyclyl, cycloalkyl, cycloalkenyl, cycloalkynyl groups may also be optionally substituted with hydrocarbyl such as alkyl, alkenyl or alkynyl.

For example, $R^{14}$ is selected from one of the following twenty-two groups:

1) hydrogen or $C_{1-5}$alkyl which may be unsubstituted or which may be substituted with one or more functional groups;

2) —$R^aX^2C(O)R^{20}$ (wherein $X^2$ represents —O— or —$NR^{21}$— (in which $R^{21}$ represents hydrogen, or alkyl optionally substituted with a functional group) and $R^{20}$ represents $C_{1-3}$alkyl, —$NR^{22}R^{23}$ or —$OR^{24}$ (wherein $R^{22}$, $R^{23}$ and $R^{24}$ which may be the same or different each represents hydrogen, or alkyl optionally substituted with a functional group);

3) —$R^bX^3R^{25}$ (wherein $X^3$ represents —O—, —C(O)—, —S—, —SO—, —$SO_2$—, —OC(O)—, —$NR^{26}C(O)$—, —$NR^{26}C(O)O$—, —$C(O)NR^{27}$—, —$C(O)ONR^{27}$—, —$SO_2NR^{28}$—, —$NR^{29}SO_2$— or —$NR^{30}$— (wherein $R^{26}$, $R^{27}$, $R^{28}$, $R^{29}$ and $R^{30}$ each independently represents hydrogen, or alkyl optionally substituted with a functional group) and $R^{25}$ represents hydrogen, hydrocarbyl (as defined herein) or a saturated heterocyclic group, wherein the hydrocarbyl or heterocyclic groups may be optionally substituted by one or more functional groups and the heterocyclic groups may additionally be substituted by a hydrocarbyl group);

4) —$R^cX^4R^aX^5R^{31}$ (wherein $X^4$ and $X^5$ which may be the same or different are each —O—, —C(O)—, —S—, —SO—, —$SO_2$—, —OC(O)—, —$NR^{32}C(O)$—, —$NR^{32}C(O)O$— —$C(O)NR^{33}$—$C(O)ONR^{33}$—, —$SO_2NR^{34}$—, —$NR^{35}SO_2$— or —$NR^{36}$— (wherein $R^{32}$, $R^{33}$, $R^{34}$, $R^{35}$ and $R^{36}$ each independently represents hydrogen or alkyl optionally substituted by a functional group) and $R^{31}$ represents hydrogen, or alkyl optionally substituted by a functional group;

5) $R^{37}$ wherein $R^{37}$ is a $C_{3-6}$cycloalkyl or saturated heterocyclic ring (linked via carbon or nitrogen), which cycloalkyl or heterocyclic group may be substituted by one or more functional groups or by a hydrocarbyl or heterocyclyl group which hydrocarbyl or heterocyclyl group may be optionally substituted by one or more functional groups;

6) —$R^dR^{37}$ (wherein $R^{37}$ is as defined hereinbefore);

7) —$R^eR^{37}$ (wherein $R^{37}$ is as defined hereinbefore);

8) —$R^fR^{37}$ (wherein $R^{37}$ is as defined hereinbefore);

9) $R^{38}$ (wherein $R^{38}$ represents a pyridone group, an aryl group or an aromatic heterocyclic group (linked via carbon or nitrogen) with 1–3 heteroatoms selected from O, N and S, which pyridone, aryl or aromatic heterocyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups;

10) —$R^gR^{38}$ (wherein $R^{38}$ is as defined hereinbefore);

11) —$R^hR^{38}$ (wherein $R^{38}$ is as defined hereinbefore);

12) —$R^iR^{38}$ (wherein $R^{38}$ is as defined hereinbefore);

13) —$R^jX^6R^{38}$ (wherein $X^6$ represents —O—, —S—, —SO—, —$SO_2$—, —OC(O)—, —$NR^{43}C(O)$—, —$NR^{43}C(O)O$—, —$C(O)NR^{44}$—, —$C(O)ONR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, or alkyl optionally substituted with a functional group) and $R^{38}$ is as defined hereinbefore);

14) —$R^kX^7R^{38}$ (wherein $X^7$ represents —O—, —C(O)—, —S—, —SO—, —$SO_2$—, —OC(O)—, —$NR^{48}C(O)$—, $NR^{48}C(O)O$—, —$C(O)NR^{49}$—, —$C(O)ONR^{49}$—, —$SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, or alkyl optionally substituted with a functional group) and $R^{38}$ is as defined hereinbefore);

15) —$R^mX^8R^{38}$ (wherein $X^8$ represents —O—, —C(O)—, —S—, —SO—, —$SO_2$—, —OC(O)—, —$NR^{53}C(O)$—, —$NR^{53}C(O)O$—, —$C(O)NR^{54}$—, —$C(O)ONR^{54}$—, —$SO_2NR^{55}$—, —$NR^{56}SO_2$— or —$NR^{57}$— (wherein $R^{53}$, $R^{54}$, $R^{55}$, $R^{56}$ and $R^{57}$ each independently represents hydrogen, hydrogen, or alkyl optionally substituted with a functional group) and $R^{38}$ is as defined hereinbefore);

16) —$R''X^9R''R^{38}$ (wherein $X^9$ represents —O—, —C(O)—, —S—, —SO—, —$SO_2$—, —OC(O)—, —$NR^{58}C(O)$—, —$NR^{58}C(O)O$—, —$C(O)NR^{59}$—, —$C(O)ONR^{59}$—, —$SO_2NR^{60}$—, —$NR^{61}SO_2$— or —$NR^{62}$— (wherein $R^{58}$, $R^{59}$, $R^{60}$, $R^{61}$ and $R^{62}$ each independently represents hydrogen, hydrogen, or alkyl optionally substituted with a functional group) and $R^{38}$ is as defined hereinbefore);

17) —$R^pX^9$—$R^{p'}R^{37}$ (wherein $X^9$ and $R^{37}$ are as defined hereinbefore);

18) $C_{2-5}$alkenyl which may be unsubstituted or which may be substituted with one or more functional groups;

19) $C_{2-5}$alkynyl which may be unsubstituted or which may be substituted with one or more functional groups;

20) —$R^tX^9R^{t'}R^{37}$ (wherein $X^9$ and $R^{37}$ are as defined hereinbefore);

21) —$R^uX^9R^{u'}R^{37}$ (wherein $X^9$ and $R^{37}$ are as defined hereinbefore); and 22) —$R^vR^{63}(R^{v'})_q(X^9)_rR^{64}$ (wherein $X^9$ is as defined hereinbefore, q is 0 or 1, r is 0 or 1, and $R^{63}$ is a $C_{1-3}$alkylene group or a cyclic group selected from divalent cycloalkyl or heterocyclic group, which $C_{1-3}$alkylene group may be substituted by one or more functional groups and which cyclic group may be substituted by one or more functional groups or by a hydrocarbyl group optionally substituted by one or more functional groups or heterocyclyl groups, or by a heterocyclyl group optionally subsituted by one or more functional groups or hydrocarbyl groups; and $R^{64}$ is hydrogen, $C_{1-3}$alkyl, or a cyclic group selected from cycloalkyl or heterocyclic group, which $C_{1-3}$alkyl group may be substituted by one or more functional groups and which cyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups;

and wherein $R^a$, $R^b$, $R^c$, $R^{c'}$, $R^d$, $R^g$, $R^j$, $R^n$, $R^{n'}$, $R^p$, $R^{p1}$, $R^{t'}$, $R^{u'}$, $R^v$ and $R^{v'}$ are independently selected from $C_{1-8}$alkylene groups optionally substitued by one or more functional groups, $R^e$, $R^h$, $R^k$ and $R^t$ are independently selected from $C_{2-8}$alkenylene groups optionally substituted by one or more functional groups, and $R^f$, $R^i$, $R^m$ and $R^u$ are independently selected from $C_{2-8}$alkynylene groups optionally substituted by one or more functional groups).

Particular examples of the twenty-two groups for $R^{14}$ are:

1) hydrogen or $C_{1-5}$alkyl which may be unsubstituted or which may be substituted with one or more groups selected from hydroxy, oxiranyl, fluoro, chloro, bromo and amino (including $C_{1-3}$alkyl and trifluoromethyl);

2) —$R^a X^2 C(O)R^{20}$ (wherein $X^2$ represents —O— or —$NR^{21}$— (in which $R^{21}$ represents hydrogen, $C_{1-3}$alkyl or $C_{1-3}$alkoxy$C_{2-3}$alkyl) and $R^{20}$ represents $C_{1-3}$alkyl, —$NR^{22}R^{23}$ or —$OR^{24}$ (wherein $R^{22}$, $R^{23}$ and $R^{24}$ which may be the same or different each represents hydrogen, $C_{1-5}$alkyl, hydroxy $C_{1-5}$alkyl or $C_{1-3}$alkoxy$C_{2-3}$alkyl);

3) —$R^b X^3 R^{25}$ (wherein $X^3$ represents —O—, —C(O)—, —S—, —SO—, —$SO_2$—, —OC(O)—, —$NR^{26}$C(O)—, —$NR^{26}$C(O)O—, —C(O)$NR^{27}$—, —C(O)O$NR^{27}$—, —$SO_2NR^{28}$—, —$NR^{29}SO_2$— or —$NR^{30}$— (wherein $R^{26}$, $R^{27}$, $R^{28}$, $R^{29}$ and $R^{30}$ each independently represents hydrogen, $C_{1-3}$alkyl, hydroxy $C_{1-3}$alkyl or $C_{1-3}$alkoxy$C_{2-3}$alkyl and s is 1 or 2) and $R^{25}$ represents hydrogen, $C_{1-6}$alkyl, $C_{2-6}$alkenyl, or a cyclic groups selected from cyclopropyl, cyclobutyl, cyclopentyl, cyclohexyl, phenyl or a 5–6-membered saturated heterocyclic group with 1–2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, di-$C_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl $C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkanoyl, $C_{1-4}$alkylamino$C_{1-4}$alkoxy, di($C_{1-4}$alkyl)amino$C_{1-4}$alkoxy and a group —(—O—)$_f(R^{b'})_g$D (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);

4) —$R^c X^4 R^{c'} X^5 R^{31}$ (wherein $X^4$ and $X^5$ which may be the same or different are each —O—, —C(O)—, —S—, —SO—, —$SO_2$—, —$NR^{32}$C(O)—, —$NR^{32}$C(O)O—, —C(O)$NR^{33}$—, C(O)O$NR^{33}$—, —$SO_2NR^{34}$—, —$NR^{35}SO_2$— or —$NR^{36}$— (wherein $R^{32}$, $R^{33}$, $R^{34}$, $R^{35}$ and $R^{36}$ each independently represents hydrogen, $C_{1-3}$alkyl, hydroxy$C_{1-3}$alkyl or $C_{1-3}$alkoxy$C_{2-3}$alkyl) and $R^{31}$ represents hydrogen, $C_{1-3}$alkyl, hydroxy $C_{1-3}$alkyl or $C_{1-3}$alkoxy$C_{2-3}$alkyl);

5) $R^{37}$ (wherein $R^{37}$ is a 4–6-membered cycloalkyl or saturated heterocyclic ring (linked via carbon or nitrogen) with 1–2 heteroatoms, selected independently from O, S and N, which cycloalkyl or heterocyclic group may bear 1 or 2 substituents selected from oxo, hydroxy, halogeno, cyano, $C_{1-4}$alkyl, hydroxy$C_{1-4}$alkyl, cyano $C_{1-4}$alkyl, cyclopropyl, $C_{1-4}$alkylsulphonyl$C_{1-4}$alkyl, $C_1$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy nitro, amino, $C_{1-4}$alkoxy, $C_{1-4}$hydroxyalkoxy, carboxy, trifluoromethyl, —C(O)$NR^{69}R^{70}$, —$NR^{71}$C(O)$R^{42}$ (wherein $R^{69}$, $R^{70}$, $R^{71}$ and $R^{72}$, which may be the same or different, each represents hydrogen, $C_{1-4}$alkyl, hydroxy $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);

6) —$R^d R^{37}$ (wherein $R^{37}$ is as defined hereinbefore);

7) —$R^e R^{37}$ (wherein $R^{37}$ is as defined hereinbefore);

8) —$R^f R^{37}$ (wherein $R^{37}$ is as defined hereinbefore);

9) $R^{38}$ (wherein $R^{38}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$alkyl, cyclopropyl, $C_{1-4}$alkylsulphonyl $C_{1-4}$alkyl, $C_{1-4}$alkoxycarbonyl, di($C_{1-4}$alkyl)amino, $C_{1-4}$alkylamino $C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxy, carboxamido, trifluoromethyl, cyano, —C(O)$NR^{39}R^{40}$, —$NR^{41}$C(O)$R^{42}$ (wherein $R^{39}$, $R^{40}$, $R^{41}$ and $R^{42}$, which may be the same or different, each represents hydrogen, $C_{1-4}$alkyl, hydroxy $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);

10) —$R^g R^{38}$ (wherein $R^{38}$ is as defined hereinbefore);

11) —$R^h R^{38}$ (wherein $R^{38}$ is as defined hereinbefore);

12) —$R^i R^{38}$ (wherein $R^{38}$ is as defined hereinbefore);

13) —$R^j X^6 R^{38}$ (wherein $X^6$ represents —O—, —C(O)—, —S—, —SO—, —$SO_2$—, —OC(O)—, —$NR^{43}$C(O)—, —$NR^{43}$C(O)O—, —C(O)$NR^{44}$—, —C(O)O$NR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, $C_{1-3}$alkyl, hydroxy $C_{1-3}$alkyl or $C_{1-3}$alkoxy$C_{2-3}$alkyl) and $R^{38}$ is as defined hereinbefore);

14) —$R^k X^7 R^{38}$ (wherein $X^7$ represents —O—, —C(O)—, —S—, —SO—, —$SO_2$—, —$NR^{48}$C(O)—, —$NR^{48}$C(O)O—, —C(O)$NR^{49}$—, —C(O)O$NR^{49}$—, —$SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, $C_{1-3}$alkyl, hydroxy$C_{1-3}$alkyl or $C_{1-3}$alkoxy$C_{2-3}$alkyl) and $R^{38}$ is as defined hereinbefore);

15) —R'''X⁸R³⁸ (wherein X⁸ represents —O—, —C(O)—, —S—, —SO—, —SO₂—, —NR⁵³C(O)—, —NR⁵³C(O)O—, —C(O)NR⁵⁴—, —C(O)ONR⁵⁴—, —SO₂NR⁵⁵—, —NR⁵⁶SO₂— or —NR⁵⁷ (wherein R⁵³, R⁵⁴, R⁵⁵, R⁵⁶ and R⁵⁷ each independently represents hydrogen, $C_{1-3}$alkyl, hydroxy $C_{1-3}$alkyl or $C_{1-3}$alkoxy $C_{2-3}$alkyl) and R³⁸ is as defined hereinbefore);

16) —R''X⁹R'''R³⁸ (wherein X⁹ represents —O—, —C(O)—, —S—, —SO—, —SO₂—, —NR⁵⁸C(O)— NR⁵⁸C(O)O—, —C(O)NR⁵⁹—, —C(O)ONR⁵⁹—, —SO₂NR⁶⁰—, —NR⁶¹SO₂— or —NR⁶²— (wherein R⁵⁸, R⁵⁹, R⁶⁰, R⁶¹ and R⁶² each independently represents hydrogen, $C_{1-3}$alkyl, hydroxy$C_{1-3}$alkyl or $C_{1-3}$alkoxy$C_{2-3}$alkyl) and R³⁸ is as defined hereinbefore);

17) —RᵖX⁹—Rᵖ'R³⁷ (wherein X⁹ and R³⁷ are as defined hereinbefore);

18) $C_{2-5}$alkenyl which may be unsubstituted or which may be substituted with one or more groups selected from hydroxy, fluoro, amino, $C_{1-4}$alkylamino, carboxy (and particularly alkyl esters thereof,) N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) —R'X⁹R'R³⁷ (wherein X⁹ and R³⁷ are as defined hereinbefore);

21) —R''X⁹R''R³⁷ (wherein X⁹ and R³⁷ are as defined hereinbefore); and

22) —R'R⁶³(Rᵛ')_q(X⁹)_rR⁶⁴ (wherein X⁹ is as defined hereinbefore, q is 0 or 1, r is 0 or 1, and R⁶³ is a $C_{1-3}$alkylene group or a cyclic group selected from cyclopropylene, cyclobutylene, cyclopentylene, cyclohexylene or a 5–6-membered saturated heterocyclic group with 1–2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl $C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)_f($C_{1-4}$alkyl)_gringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl); and R⁶⁴ is hydrogen, $C_{1-3}$alkyl, or a cyclic group selected from cyclopropyl, cyclobutyl, cyclopentyl, cyclohexyl and a 5–6-membered saturated or unsaturated heterocyclic group with 1–2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)_f($C_{1-4}$alkyl)_gringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);

and wherein Rᵃ, Rᵇ, Rᵇ', Rᶜ, Rᶜ', Rᵈ, Rᵍ, Rʲ, Rⁿ, Rⁿ', Rᵖ, Rᵖ¹, Rᵗ', Rᵘ', Rᵛ and Rᵛ' are independently selected from $C_{1-8}$alkylene groups optionally substitued by one or more substituents selected from hydroxy, halogeno and amino, Rᵉ Rʰ, Rᵏ and Rᵗ are independently selected from $C_{2-8}$alkenylene groups optionally substituted by one or more substituents selected from hydroxy, halogeno and amino, and Rᵗ may additionally be a bond;

Rᶠ, Rⁱ, Rᵐ and Rᵘ are independently selected from $C_{2-5}$alkynylene groups optionally substituted by one or more substituents selected from hydroxy, halogeno and amino.

In particular R¹, R², R³, R⁴ are independently selected from, halogeno, cyano, nitro, trifluoromethyl, $C_{1-3}$alkyl, $C_{1-3}$alkoxy, $C_{1-3}$alkylsulphanyl, —NR¹²R¹³ (wherein R¹² and R¹³, which may be the same or different, each represents hydrogen, or $C_{1-3}$alkyl and one of R¹² or R¹³ may additionally be hydroxy), or R¹⁴X¹— wherein X¹ represents a direct bond, —O—, —CH₂—, —OC(O)—, —C(O)—, —S—, —SO—, —SO₂—, —NR¹⁵C(O)—, —C(O)NR¹⁶—, —SO₂NR¹⁷—, —NR¹⁸SO₂— or —NR¹⁹— (wherein R¹⁵, R¹⁶, R¹⁷, R¹⁸ and R¹⁹ each independently represents hydrogen, $C_{1-3}$alkyl or $C_{1-3}$alkoxy$C_{2-3}$alkyl), and R¹⁴ is selected from one of the following groups:

1') hydrogen or $C_{1-5}$alkyl which may be unsubstituted or which may be substituted with one or more groups selected from hydroxy, fluoro or amino, 2') $C_{1-5}$alkylX²COR²⁰ (wherein X² represents —O— or —NR²¹ (in which R²⁰ represents hydrogen, $C_{1-3}$alkyl or $C_{1-3}$alkoxy$C_{2-3}$alkyl) and R²¹ represents $C_{1-3}$alkyl, —NR²²R²³ or —OR²⁴ (wherein R²², R²³ and R²⁴ which may be the same or different each represents hydrogen, $C_{1-3}$alkyl or $C_{1-3}$alkoxy$C_{2-3}$alkyl));

3') $C_{1-5}$alkylX³R²⁵ (wherein X³ represents —O—, —S—, —SO—, —SO₂—, —OCO—, —NR²⁶CO—, —CONR²⁷—, —SO₂NR²⁸—, —NR²⁹SO₂— or —NR³⁰— (wherein R²⁶, R²⁷, R²⁸, R²⁹ and R³⁰ each independently represents hydrogen, $C_{1-3}$alkyl or $C_{1-3}$alkoxy$C_{2-3}$alkyl) and R²⁵ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkylX⁴$C_{1-5}$alkylX⁵R³¹ (wherein X⁴ and X⁵ which may be the same or different are each —O—, —S—, —SO—, —SO₂—, —NR³²CO—, —CONR³³—, —SO₂NR³⁴—, —NR³⁵SO₂— or NR³⁶— (wherein R³², R³³, R³⁴, R³⁵ and R³⁶ each independently represents hydrogen, $C_{1-3}$alkyl or $C_{1-3}$alkoxy$C_{2-3}$alkyl) and R³¹ represents hydrogen or $C_{1-3}$alkyl);

5') R³⁷ (wherein R³⁷ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl $C_{1-3}$alkyl);

6') $C_{1-5}$alkyl$R^{37}$ (wherein $R^{37}$ is as defined hereinbefore in (5'));

7') $C_{2-5}$alkenyl$R^{37}$ (wherein $R^{37}$ is as defined hereinbefore in (5'));

8') $C_{2-5}$alkynyl$R^{37}$ (wherein $R^{37}$ is as defined hereinbefore in (5'));

9') $R^{38}$ (wherein $R^{38}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —CONR$^{39}$R$^{40}$ and —NR$^{41}$COR$^{42}$ (wherein R$^{39}$, R$^{40}$, R$^{41}$ and R$^{42}$, which may be the same or different, each represents hydrogen, $C_{1-4}$alkyl or $C_{1-3}$alkoxy$C_{2-3}$alkyl));

10') $C_{1-5}$alkyl$R^{38}$ (wherein $R^{38}$ is as defined hereinbefore in (9'));

11') $C_{2-5}$alkenyl$R^{38}$ (wherein $R^{38}$ is as defined hereinbefore in (9'));

12') $C_{2-5}$alkynyl$R^{38}$ (wherein $R^{38}$ is as defined hereinbefore in (9'));

13') $C_{1-5}$alkyl$X^{6}R^{38}$ (wherein $X^{6}$ represents —O—, —S—, —SO—, —SO$_2$—, —NR$^{43}$CO—, —CONR$^{44}$—, —SO$_2$NR$^{45}$—, NR$^{46}$SO$_2$— or —NR$^{47}$— (wherein R$^{43}$, R$^{44}$, R$^{45}$, R$^{46}$ and R$^{47}$ each independently represents hydrogen, $C_{1-3}$alkyl or $C_{1-3}$alkoxy$C_{2-3}$alkyl) and $R^{38}$ is as defined hereinbefore in (9'));

14') $C_{2-5}$alkenyl$X^{7}R^{38}$ (wherein $X^{7}$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— (wherein R$^{48}$, R$^{49}$, R$^{50}$, R$^{51}$ and R$^{52}$ each independently represents hydrogen, $C_{1-3}$alkyl or $C_{1-3}$alkoxy$C_{2-3}$alkyl) and $R^{38}$ is as defined hereinbefore in (9'));

15') $C_{2-5}$alkynyl$X^{8}R^{38}$ (wherein $X^{8}$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{57}$— (wherein R$^{53}$, R$^{54}$, R$^{55}$, R$^{56}$ and R$^{57}$ each independently represents hydrogen, $C_{1-3}$alkyl or $C_{1-3}$alkoxy$C_{2-3}$alkyl) and $R^{38}$ is as defined hereinbefore in (9'));

16') $C_{1-3}$alkyl$X^{9}C_{1-3}$alkyl$R^{38}$ (wherein $X^{9}$ represents —O—, —S—, —SO—, —SO$_2$—, —NR$^{58}$CO—, —CONR$^{59}$—, —SO$_2$NR$^{60}$—, —NR$^{61}$SO$_2$— or —NR$^{62}$— (wherein R$^{58}$, R$^{59}$, R$^{60}$, R$^{61}$ and R$^{62}$ each independently represents hydrogen, $C_{1-3}$alkyl or $C_{1-3}$alkoxy$C_{2-3}$alkyl) and $R^{38}$ is as defined hereinbefore in (9')); and 17') $C_{1-3}$alkyl$X^{9}C_{1-3}$alkyl$R^{37}$ (wherein $X^{9}$ and $R^{37}$ are as defined hereinbefore (in 5')).

Particular examples of compounds of formula (I) are compounds of formula (II)

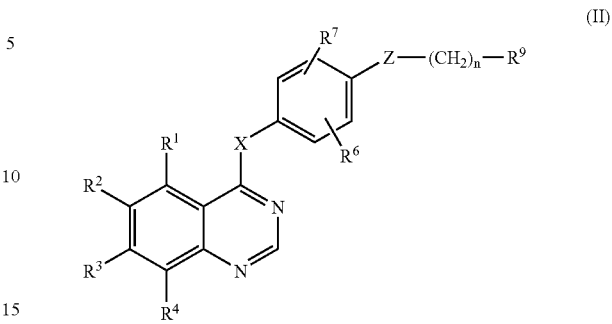

or a salt, ester, amide or prodrug thereof;

where X, Z, n, $R^9$, $R^6$, $R^7$, $R^1$, $R^2$, $R^3$ and $R^4$ are as defined in relation to formula (I).

In a particular embodiment, the invention provides the use of a compound of formula (IIA) which has the structure (II) as shown above, or a salt, ester or amide thereof; and where X is O, or S, S(O) or S(O)$_2$, or NR$^8$ where R$^8$ is hydrogen or $C_{1-6}$alkyl;

Z is O or S, n is 0, or an integer of from 1 to 6

$R^9$ is hydrogen or optionally substituted hydrocarbyl or optionally substituted heterocyclyl;

and $R^6$ and $R^7$ are independently selected from hydrogen, halo, $C_{1-4}$alkyl, $C_{1-4}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and $R^1$, $R^2$, $R^3$, $R^4$ are independently selected from, halo, cyano, nitro, trifluoromethyl, $C_{1-3}$alkyl, —NR$^9$R$^{10}$ (wherein R$^9$ and R$^{10}$, which may be the same or different, each represents hydrogen or $C_{1-3}$alkyl), or —X$^1$R$^{14}$ wherein X$^1$ represents a direct bond, —O—, —CH$_2$—, —OCO—, carbonyl, —S—, —SO—, —SO$_2$—, —NR$^{12}$CO—, —CONR$^{12}$—, —SO$_2$NR$^{12}$—, —NR$^{13}$SO$_2$— or —NR$^{14}$— (wherein R$^{12}$, R$^{13}$ and R$^{14}$ each independently represents hydrogen, $C_{1-3}$alkyl or $C_{1-3}$alkoxy$C_{2-3}$alkyl), and R$^{14}$ is selected from one of the following groups: 1') hydrogen or $C_{1-5}$alkyl which may be unsubstituted or which may be substituted with one or more groups selected from hydroxy, fluoro or amino, 2') $C_{1-5}$alkyl$X^2COR^{20}$ (wherein $X^2$ represents —O— or —$NR^{21}$— (in which $R^{20}$ represents hydrogen, $C_{1-3}$alkyl or $C_{1-3}$alkoxy$C_{2-3}$alkyl) and $R^{21}$ represents $C_{1-3}$alkyl, —$NR^{22}R^{23}$ or —$OR^{24}$ (wherein $R^{22}$, $R^{23}$ and $R^{24}$ which may be the same or different each represents hydrogen, $C_{1-3}$alkyl or $C_{1-3}$alkoxy$C_{2-3}$alkyl));

3') $C_{1-5}$alkyl$X^3R^{25}$ (wherein $X^3$ represents —O—, —S—, —SO—, —$SO_2$—, —OCO—, —$NR^{26}CO$—, $CONR^{27}$—, —$SO_2NR^{28}$—, —$NR^{29}SO_2$— or —$NR^{30}$— (wherein $R^{26}$, $R^{27}$, $R^{28}$, $R^{29}$ and $R^{30}$ each independently represents hydrogen, $C_{1-3}$alkyl or $C_{1-3}$alkoxy $C_{2-3}$alkyl) and $R^{25}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{31}$ (wherein $X^4$ and $X^5$ which may be the same or different are each —O—, —S—, —SO—, —$SO_2$—, —$NR^{32}CO$—, —$CONR^{33}$—, —$SO_2NR^{34}$—, —$NR^{35}SO_2$— or $NR^{36}$— (wherein $R^{32}$, $R^{33}$, $R^{34}$, $R^{35}$ and $R^{36}$ each independently represents hydrogen, $C_{1-3}$alkyl or $C_{1-3}$alkoxy$C_{2-3}$alkyl) and $R^{31}$ represents hydrogen or $C_{1-3}$alkyl);

5') $R^{37}$ (wherein $R^{37}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy $C_{1-4}$alkyl and $C_{1-4}$alkylsulphonyl$C_{1-4}$alkyl);

6') $C_{1-5}$alkyl$R^{37}$ (wherein $R^{37}$ is as defined hereinbefore in (5'));

7') $C_{2-5}$alkenyl$R^{37}$ (wherein $R^{37}$ is as defined hereinbefore in (5'));

8') $C_{2-5}$alkynyl$R37$ (wherein $R^{37}$ is as defined hereinbefore in (5'));

9') $R^{38}$ (wherein $R^{38}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{39}R^{40}$ and —$NR^{41}COR^{42}$ (wherein $R^{39}$, $R^{40}$, $R^{41}$ and $R^{42}$, which may be the same or different, each represents hydrogen, $C_{1-4}$alkyl or $C_{1-3}$alkoxy$C_{2-3}$alkyl));

10') $C_{1-5}$alkyl$R^{38}$ (wherein $R^{38}$ is as defined hereinbefore in (9'));

11') $C_{2-5}$alkenyl$R^{38}$ (wherein $R^{38}$ is as defined hereinbefore in (9'));

12') $C_{2-5}$alkynyl$R^{38}$ (wherein $R^{38}$ is as defined hereinbefore in (9'));

13') $C_{1-5}$alkyl$X^6R^{38}$ (wherein $X^6$ represents —O—, —S—, —SO—, —$SO_2$—, —$NR^{43}CO$—, —$CONR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{38}$ is as defined hereinbefore in (9'));

14') $C_{2-5}$alkenyl$X^7R^{38}$ (wherein $X^7$ represents —O—, —S—, —SO—, —$SO_2$—, —$NR^{48}CO$—, —$CONR^{49}$—, —$SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl) and $R^{38}$ is as defined hereinbefore in (9'));

15') $C_{2-5}$alkynyl$X^8R^{38}$ (wherein $X^8$ represents —O—, —S—, —SO—, —$SO_2$—, —$NR^{53}CO$—, —$CONR^{54}$—, —$SO_2NR^{15}$—, —$NR^{56}SO_2$— or —$NR^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{38}$ is as defined hereinbefore in (9'));

16') $C_{1-3}$alkyl$X^9C_{1-3}$alkyl$R^{38}$ (wherein $X^9$ represents —O—, —S—, —SO—, —$SO_2$—, —$NR^{58}CO$—, —$CONR^{59}$—, —$SO_2NR^{60}$—, —$NR^{61}SO_2$— or —$NR^{62}$— (wherein $R^{58}$, $R^{59}$, $R^{60}$, $R^{61}$ and $R^{62}$ each independently represents hydrogen, $C_{1-3}$alkyl or $C_{1-3}$alkoxy$C_{2-3}$alkyl) and $R^{38}$ is as defined hereinbefore in (9')); and 17') $C_{1-3}$alkyl$X^9C_{1-3}$alkyl$R^{37}$ (wherein $X^9$ and $R^{37}$ are as defined hereinbefore (in 5')) in the preparation of a medicament for use in the inhibition of aurora 2 kinase.

Preferably $R^1$ is hydrogen. Suitably $R^4$ is hydrogen or a small substituent such as halo, $C_{1-4}$ alkyl or $C_{1-4}$alkoxy such as methoxy.

Preferably both $R^1$ and $R^4$ are hydrogen.

In a preferred embodiment, at least one group $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Preferably in this case, $X^1$ is oxygen and $R^{14}$ includes a methylene group directly adjacent $X^1$. Preferably where bridging alkylene, alkenylene or alkynylene groups $R^a$, $R^b$, $R^{b'}$, $R^c$, $R^{c'}$, $R^d$, $R^g$, $R^j$, $R^n$, $R^{n'}$, $R^p$, $R^{t'}$, $R^{u'}$, $R^v$, $R^{v'}$, $R^e$, $R^h$, $R^k$, $R^t$, $R^f$, $R^i$, $R^m$ and $R^u$ are present, at least one such group includes a substituent and in particular a hydroxy substituent.

In particular $R^{14}$ is selected from a group of formula (I), (3), (6), (10) or (22) above and preferably selected from groups (1) or (10) above. Particular groups $R^{14}$ are those in group (1) above, especially alkyl such as methyl or halo subsituted alkyl, or those in group (10) above. In one suitable embodiment, at least one of $R^2$ or $R^3$ is a group $OC^{1-5}$alkyl$R^{37}$ and $R^{37}$ is a heterocyclic ring such as an N-linked morpholine ring such as 3-morpholinopropoxy.

Other preferred groups for $R^3$ are groups of formula (3) above in particular those where $X^3$ is —$NR^{30}$—.

Suitably $R^2$ is selected from, halo, cyano, nitro, trifluoromethyl, $C_{1-3}$alkyl, —$NR^{12}R^{13}$ (wherein $R^{12}$ and $R^{13}$, which may be the same or different, each represents hydrogen or $C_{1-3}$alkyl), or a group —$X^1R^{14}$. Preferred examples of —$X^1R^{14}$ for $R^2$ include those listed above in relation to $R^3$.

Other examples for $R^2$ and $R^3$ include methoxy or 3,3,3-trifluoroethoxy.

Preferably X is NH or O and is most preferably NH.

Suitably $R^9$ is hydrogen, optionally substituted alkenyl, optionally substituted aryl or optionally substituted heterocyclyl. In particular, $R^9$ is hydrogen, ethenyl, optionally subsituted phenyl, optionally substituted pyridyl or optionally substituted furanyl, and in particular hydrogen, ethenyl, optionally subsituted phenyl or optionally substituted pyridyl. Suitable optional substitutents for $R^9$ groups include $C_{1-3}$alkoxy such as methoxy, $C_{1-3}$alkyl such as methyl, halo such as chloro, or nitro and in particular $C_{1-3}$alkoxy such as methoxy or $C_{1-3}$alkyl such as methyl.

Preferably n is 0 when $R^9$ is optionally subsituted phenyl or naphthyl. When $R^9$ is hydrogen, n is suitably other than 0 and preferably from 1 to 5, more preferably from 3 to 5.

Other examples of compounds of formula (I) are compounds of formula (III)

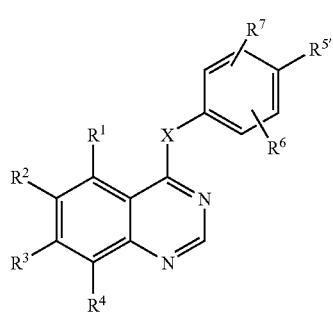

(III)

or salts, esters, amides or prodrugs thereof;

where X, $R^1$, $R^2$, $R^3$, $R^4$, $R^6$ and $R^7$ are as defined in relation to formula (I) and $R^{5'}$ is an optionally subsitituted hydrocarbyl, optionally substituted heterocyclyl or optionally substituted alkoxy group, provided that $R^{5'}$ is other than ethenyl substituted by a carboxy group or an amide or sulphonamide derivative thereof.

Particular examples of $R^{5'}$ include $C_{1-6}$alkyl, optionally substituted by a functional group, in particular by carboxy or an $C_{1-6}$alkyl ester thereof, or cyano, or by an aryl group such as phenyl which may itself be substituted by a functional group. A further particular example of $R^{5'}$ is benzyl and cyanobenzyl.

Another example of $R^{5'}$ is optionally substituted aryl such as phenyl, where the optional substituents include $C_{1-3}$alkyl groups as well as functional groups in particular nitro and halo such as bromo, Further examples of $R^{5'}$ groups include $C_{2-6}$alkynyl in particular ethynyl, which may be optionally substituted for example with trimethylsilyl groups or by carboxy or an $C_{1-6}$alkyl ester thereof.

In a further embodiment, the invention provides the use of a compound of formula (IIIA) which is of structure (III) as shown above, or a salt, ester or amide thereof; and where X is O, or S, S(O) or S(O)$_2$, or $NR^8$ where $R^8$ is hydrogen or $C_{1-6}$alkyl;

$R^{5'}$ is hydrogen or optionally substituted hydrocarbyl or optionally substituted heterocyclyl;

and $R^6$ and $R^7$ are independently selected from hydrogen, halo, $C_{1-4}$alkyl, $C_{1-4}$ alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$ alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and $R^1$, $R^2$, $R^3$, $R^4$ are independently selected from, halo, cyano, nitro, trifluoromethyl, $C_{1-3}$alkyl, —$NR^9R^{10}$ (wherein $R^9$ and $R^{10}$, which may be the same or different, each represents hydrogen or $C_{1-3}$alkyl), or —$X^1R^{14}$ (wherein $X^1$ represents a direct bond, —O—, —$CH_2$—, —OCO—, carbonyl, —S—, —SO—, —$SO_2$—, —$NR^{12}CO$—, —$CONR^{12}$—, —$SO_2NR^{12}$—, —$NR^{13}SO_2$— or —$NR^{14}$— (wherein $R^{12}$, $R^{13}$ and $R^{14}$ each independently represents hydrogen, $C_{1-3}$alkyl or $C_{1-3}$alkoxy$C_{2-3}$alkyl), and $R^{14}$ is selected from one of the following groups:

1') hydrogen or $C_{1-5}$alkyl which may be unsubstituted or which may be substituted with one or more groups selected from hydroxy, fluoro or amino, 2') $C_{1-5}$alkyl$X^2COR^{20}$ (wherein $X^2$ represents —O— or —$NR^{21}$— (in which $R^{20}$ represents hydrogen, $C_{1-3}$alkyl or $C_{1-3}$alkoxy$C_{2-3}$alkyl) and $R^{21}$ represents $C_{1-3}$alkyl, —$NR^{22}R^{23}$ or —$OR^{24}$ (wherein $R^{22}$, $R^{23}$ and $R^{24}$ which may be the same or different each represents hydrogen, $C_{1-3}$alkyl or $C_{1-3}$alkoxy$C_{2-3}$alkyl));

3') $C_{1-5}$alkyl$X^3R^{25}$ (wherein $X^3$ represents —O—, —S—, —SO—, —$SO_2$—, —OCO—, —$NR^{26}CO$—, —$CONR^{27}$—, —$SO_2NR^{28}$—, —$NR^{29}SO_2$— or —$NR^{30}$— (wherein $R^{26}$, $R^{27}$, $R^{28}$, $R^{29}$ and $R^{30}$ each independently represents hydrogen, $C_{1-3}$alkyl or $C_{1-3}$alkoxy$C_{2-3}$alkyl) and $R^{25}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{31}$ (wherein $X^4$ and $X^5$ which may be the same or different are each —O—, —S—, —SO—, —$SO_2$—, —$NR^{32}CO$—, —$CONR^{33}$—, —$SO_2NR^{34}$—, —$NR^{35}SO_2$— or —$NR^{36}$— (wherein $R^{32}$, $R^{33}$, $R^{34}$, $R^{35}$ and $R^{36}$ each independently represents hydrogen, $C_{1-3}$alkyl or $C_{1-3}$alkoxy$C_{2-3}$alkyl) and $R^{31}$ represents hydrogen or $C_{1-3}$alkyl);

5') $R^{37}$ (wherein $R^{37}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$ alkyl);

6') $C_{1-5}$alkyl$R^{37}$ (wherein $R^{37}$ is as defined hereinbefore in (5'));

7') $C_{2-5}$alkenyl$R^{37}$ (wherein $R^{37}$ is as defined hereinbefore in (5'));

8') C$_{2-5}$alkynylR$^{37}$ (wherein R$^{37}$ is as defined hereinbefore in (5'));

9') R$^{38}$ (wherein R$^{38}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —CONR$^{39}$R$^{40}$ and —NR$_4$COR$^{42}$ (wherein R$^{39}$, R$^{40}$, R$^{41}$ and R$^{42}$, which may be the same or different, each represents hydrogen, C$_{1-4}$alkyl or C$_{1-3}$alkoxyC$_{2-3}$alkyl));

10') C$_{1-5}$alkylR$^{38}$ (wherein R$^{38}$ is as defined hereinbefore in (9'));

11') C$_{2-5}$alkenylR$^{38}$ (wherein R$^{38}$ is as defined hereinbefore in (9'));

12') C$_{2-5}$alkynylR$^{38}$ (wherein R$^{38}$ is as defined hereinbefore in (9'));

13') C$_{1-5}$alkylX$^{6}$R$^{38}$ (wherein X$^{6}$ represents —O—, —S—, —SO—, —SO$_2$—, —NR$^{43}$CO—, —CONR$^{44}$—, represents hydrogen, C$_{1-3}$alkyl or C$_{1-3}$alkoxy C$_{2-3}$alkyl) and R$^{38}$ is as defined hereinbefore in (9'));

14') C$_{2-5}$alkenylX$^{7}$R$^{38}$ (wherein X$^{7}$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— (wherein R$^{48}$, R$^{49}$, R$^{50}$, R$^{51}$ and R$^{52}$ each independently represents hydrogen, C$_{1-3}$alkyl or C$_{1-3}$alkoxy C$_{2-3}$alkyl) and R$^{38}$ is as defined hereinbefore in (9'));

15') C$_{2-5}$alkynylX$^{8}$R$^{38}$ (wherein X$^{8}$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{52}$— (wherein R$^{48}$, R$^{49}$, R$^{50}$, R$^{51}$ and R$^{52}$ each independently represents hydrogen, C$_{1-3}$alkyl or C$_{1-3}$alkoxyC$_{2-3}$alkyl) and R$^{38}$ is as defined hereinbefore in (9'));

16') C$_{1-3}$alkylX$^{9}$C$_{1-3}$alkylR$^{38}$ (wherein X$^{9}$ represents —O—, —S—, —SO—, —SO$_2$—, —NR$^{53}$CO—, —CONR$^{59}$—, —SO$_2$NR$^{60}$— or —NR$^{62}$— (wherein R$^{58}$, R$^{59}$, R$^{60}$, R$^{61}$ and R$^{62}$ each independently represents hydrogen, C$_{1-3}$alkyl or C$_{1-3}$alkoxyC$_{2-3}$alkyl) and R$^{38}$ is as defined hereinbefore in (9')); and 17') C$_{1-3}$alkylX$^{9}$C$_{1-3}$alkylR$^{37}$ (wherein X$^{9}$ and R$^{37}$ are as defined hereinbefore (in 5') in the preparation of a medicament for use in the inhibition of aurora 2 kinase.

In yet a further embodiment, compounds of formula (I) are compounds of formula (IV)

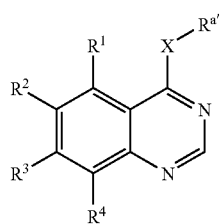

(IV)

or a salt, ester, amide or prodrug thereof;

where R$^{1}$, R$^{2}$, R$^{3}$, R$^{4}$ and X are as defined in relation to formula (I) and R$^{a'}$ is a 3-quinoline group or a group of sub-formula (i)

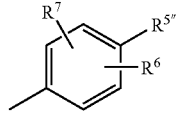

(i)

where R$^{6}$ and R$^{7}$ are as defined in relation to formula (I) and R$^{5''}$ is halogen or a group of formula NR$^{10}$R$^{10'}$ where R$^{10}$ and R$^{10'}$ are as defined above in relation to formula (I)

Examples of R$^{5''}$ include halogen such as chloro, fluoro or iodo.

Other examples of R$^{5''}$ groups include groups of formula NR$^{10}$R$^{10'}$ where R$^{10}$ and R$^{10'}$ are independently selected from hydrogen, hydrocarbyl such as alkyl or heterocyclyl, and in particular are hydrogen, hydrocarbyl and most preferably are hydrogen. Further examples of R$^{10}$ and R$^{10'}$ include groups where R$^{10}$ and R$^{10'}$ together with the nitrogen atom to which they are attached form a heterocyclic ring such as a morpholino or tetrahydropyridyl group. Yet further embodiments are compounds where R$^{5}$ is a group —N=NR$^{11}$ where R$^{11}$ is hydrocarbyl or heterocyclyl and in particular is hydrocarbyl such as alkyl or aryl such as phenyl.

In a further embodiment, the invention provides the use of a compound of formula (IVA) which is of structure (IV) as shown above, or a salt, ester or amide thereof;

where X is O, or S, S(O) or S(O)$_2$, or NR$^{8}$ where R$^{8}$ is hydrogen or C$_{1-6}$alkyl; R$^{a'}$ is a 3-quinoline group or a group of sub-formula (i)

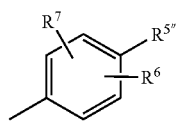

(i)

where R$^{5''}$ is halogen or a group of formula NR$^{10}$R$^{10'}$ where R$^{10}$ and R$^{10'}$ are selected from hydrogen or optionally substituted hydrocarbyl or R$^{10}$ and R$^{10'}$ together with the nitrogen atom to which they are attached form a heterocyclic ring which may optionally contain further heteroatoms or an azo group of formula —N=N—R$^{11}$ where R$^{11}$ is an optionally substituted hydrocarbyl group or optionally substituted heterocyclic group;

R$^{6}$ and R$^{7}$ are independently selected from hydrogen, halo, C$_{1-4}$alkyl, C$_{1-4}$alkoxy, C$_{1-4}$alkoxymethyl, di(C$_{1-4}$alkoxy)methyl, C$_{1-4}$alkanoyl, trifluoromethyl, cyano, amino, C$_{2-5}$alkenyl, C$_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, C$_{1-3}$alkyl, C$_{1-3}$alkoxy, C$_{1-3}$alkanoyloxy, trifluoromethyl, cyano, amino, nitro, C$_{2-4}$alkanoyl, C$_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$ alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and $R^1$, $R^2$, $R^3$, $R^4$ are independently selected from, halo, cyano, nitro, trifluoromethyl, $C_{1-3}$alkyl, —$NR^9R^{10}$ (wherein $R^9$ and $R^{10}$, which may be the same or different, each represents hydrogen or $C_{1-3}$alkyl), or —$X^1R^{14}$ (wherein $X^1$ represents a direct bond, —O—, —$CH_2$—, —OCO—, carbonyl, —S—, —SO—, —$SO_2$—, —$NR^{12}CO$—, —$CONR^{12}$—, —$SO_2NR^{12}$—, —$NR^{13}SO_2$ or —$NR^{14}$— (wherein $R^{12}$, $R^{13}$ and $R^{14}$ each independently represents hydrogen, $C_{1-3}$alkyl or $C_{1-3}$alkoxy$C_{2-3}$alkyl), and $R^{14}$ is selected from one of the following groups:

1') hydrogen or $C_{1-5}$alkyl which may be unsubstituted or which may be substituted with one or more groups selected from hydroxy, fluoro or amino, 2') $C_{1-5}$alkyl$X^2COR^{20}$ (wherein $X^2$ represents —O— or —$NR^{21}$— (in which $R^{20}$ represents hydrogen, $C_{1-3}$alkyl or $C_{1-3}$alkoxy$C_{2-3}$alkyl) and $R^{21}$ represents $C_{1-3}$alkyl, —$NR^{22}R^{23}$ or —$OR^{24}$ (wherein $R^{22}$, $R^{23}$ and $R^{24}$ which may be the same or different each represents hydrogen, $C_{1-3}$alkyl or $C_{1-3}$alkoxy$C_{2-3}$alkyl));

3') $C_{1-5}$alkyl$X^3R^{25}$ (wherein $X^3$ represents —O—, —S—, —SO—, —$SO_2$—, —OCO—, —$NR^{26}CO$—, —$CONR^{27}$—, —$SO_2NR^{28}$—, —$NR^{29}SO_2$— or —$NR^{30}$— (wherein $R^{26}$, $R^{27}$, $R^{28}$, $R^{29}$ and $R^{30}$ each independently represents hydrogen, $C_{1-3}$alkyl or $C_{1-3}$alkoxy$C_{2-3}$alkyl) and $R^{25}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{31}$ (wherein $X^4$ and $X^5$ which may be the same or different are each —O—, —S—, —SO—, —$SO_2$—, —$NR^{32}CO$—, —$CONR^{33}$—, —$SO_2NR^{34}$—, —$NR^{35}SO_2$— or $NR^{36}$— (wherein $R^{32}$, $R^{33}$, $R^{34}$, $R^{35}$ and $R^{36}$ each independently represents hydrogen, $C_{1-3}$alkyl or $C_{1-3}$alkoxy$C_{2-3}$alkyl) and $R^{31}$ represents hydrogen or $C_{1-3}$alkyl);

5') $R^{37}$ (wherein $R^{37}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$ alkyl);

6') $C_{1-5}$alkyl$R^{37}$ (wherein $R^{37}$ is as defined hereinbefore in (5'));

7') $C_{2-5}$alkenyl$R^{37}$ (wherein $R^{37}$ is as defined hereinbefore in (5'));

8') $C_{2-5}$alkynyl$R^{37}$ (wherein $R^{37}$ is as defined hereinbefore in (5'));

9') $R^{38}$ (wherein $R^{38}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_4$hydroxyalkyl, $C_{1-4}$aminoalkyl, $C_{1-4}$alkylamino, $C_4$hydroxyalkoxy, carboxy, trifluoromethyl, cyano, —$CONR^{39}R^{40}$ and —$NR^{41}COR^{42}$ (wherein $R^{39}$, $R^{40}$, $R^{41}$ and $R^{42}$, which may be the same or different, each represents hydrogen, $C_{1-4}$alkyl or $C_{1-3}$alkoxy$C_{2-3}$alkyl));

10') $C_{1-5}$alkyl$R^{38}$ (wherein $R^{38}$ is as defined hereinbefore in (9'));

11') $C_{2-5}$alkenyl$R^{38}$ (wherein $R^{38}$ is as defined hereinbefore in (9'));

12') $C_{2-5}$alkynyl$R^{38}$ (wherein $R^{38}$ is as defined hereinbefore in (9'));

13') $C_{1-5}$alkyl$X^6R^{38}$ (wherein $X^6$ represents —O—, —S—, —SO—, —$SO_2$—, —$NR^{43}CO$—, —$CONR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{38}$ is as defined hereinbefore in (9'));

14') $C_{2-5}$alkenyl$X^7R^{38}$ (wherein $X^7$ represents —O—, —S—, —SO—, —$SO_2$—, —$NR^{48}CO$—, —$CONR^{49}$—, —$SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl) and $R^{38}$ is as defined hereinbefore in (9'));

15') $C_{2-5}$alkynyl$X^8R^{38}$ (wherein $X^8$ represents —O—, —S—, —SO—, —$SO_2$—, —$NR^{53}CO$—, —$CONR^{54}$—, —$SO_2NR^{55}$—, —$NR^{56}SO_2$— or —$NR^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{38}$ is as defined hereinbefore in (9'));

16') $C_{1-3}$alkyl$X^9C_{1-3}$alkyl$R^{38}$ (wherein $X^9$ represents —O—, —S—, —SO—, —$SO_2$—, —$NR^{58}CO$—, —$CONR^{59}$—, —$SO_2NR^{60}$—, —$NR^{61}SO_2$— or —$NR^{62}$— (wherein $R^{58}$, $R^{59}$, $R^{60}$, $R^{61}$ and $R^{62}$ each independently represents hydrogen, $C_{1-4}$alkyl or $C_{1-3}$alkoxy$C_{2-3}$alkyl) and $R^{38}$ is as defined hereinbefore in (9')); and 17') $C_{1-3}$alkyl$X^9C_{1-3}$alkyl$R^{37}$ (wherein $X^9$ and $R^{37}$ are as defined hereinbefore (in 5') in the preparation of a medicament for use in the inhibition of aurora 2 kinase.

Suitably in all the above compounds, $R^6$ and $R^7$ are independently selected from hydrogen halo, $C_{1-4}$alkoxy such as methoxy, or ethoxy, cyano, trifluoromethyl, or phenyl.

Preferably $R^6$ and $R^7$ are hydrogen.

Suitable prodrugs of compounds of formula (I) are groups which enhance solubility and include phoshates and sulphates, in particular phosphates as well as alkyl, aryl or aralkyl derivatives thereof such as dibenzylphosphate. The prodrug moiety may be attached at any suitable position in the molecule, for example as a derivative of a hydroxy group, but in particular, may be advantageously present on one or more of groups $R^1$, $R^2$, $R^3$ or $R^4$, and preferably at $R^2$ or $R^3$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. Where the compound of formula (I) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy $C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of formula (I) which have a carboxy group which is derivatised into an amide such as a N—$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

Esters which are not in vivo hydrolysable may be useful as intermediates in the production of the compounds of formula (I).

Particular examples of compounds of formula (I) are set out in Tables 1–5

TABLE 1

| No | $R^5$ |
|---|---|
| 1 | n-propoxy |
| 2 | phenoxy |

TABLE 1-continued

| No | $R^5$ |
|---|---|
| 3 | benzyloxy |
| 4 | methylthio |
| 5 | n-pentoxy |
| 6 | 2-(carbomethoxy)ethyl |
| 7 | 4-nitrophenyl |
| 8 | phenyl |
| 9 | n-propyl |
| 10 | benzyl |
| 11 | 4-bromophenyl |
| 12 | 2-cyanoethyl |
| 13 | iodo |
| 14 | —N═N-phenyl |

TABLE 2

| No. | $R^5$ | $R^6$ | $R^7$ |
|---|---|---|---|
| 15 | F | F | H |
| 16 | Cl | H | phenyl |

TABLE 3

| No. | $R^3$ | $R^5$ |
|---|---|---|
| 17 | OCH$_3$ | n-butoxy |
| 18 | OCH$_3$ | OCH$_2$-(2-pyridyl) |
| 19 | OCH$_3$ | OCH$_2$CH$_2$-phenyl |
| 20 | OCH$_3$ | allyloxy |
| 21 | OCH$_3$ | OCH$_2$-(2-furyl) |
| 22 | OCH$_3$ | 2-(trimethylsilyl)ethynyl |
| 23 | OCH$_3$ | ethynyl |
| 24 | OCH$_3$ | 2-(carboethoxy)ethynyl |
| 25 | OCH$_3$ | 2-(carboethoxy)ethyl |
| 26 | OCH$_3$ | amino |
| 27 | benzyloxy | phenoxy |

TABLE 3-continued

No. | R³ | R⁵
--- | --- | ---
28 | 3-(4-morpholino)propoxy | thiomethyl
29 | 3-(4-morpholino)propoxy | phenoxy
30 | 3-(4-morpholino)propoxy | benzyloxy
31 | 3-(4-morpholino)propoxy | (4-nitrophenyl)thio
32 | 3-(4-morpholino)propoxy | n-butoxy
33 | 3-(4-morpholino)propoxy | 4-chlorophenoxy
34 | 3-(4-morpholino)propoxy | CH(CN)-phenyl
35 | 3-(4-morpholino)propoxy | n-hexyl
36 | 3-(4-morpholino)propoxy | n-butyl
37 | 3-(4-morpholino)propoxy | benzyl
38 | 3-(4-morpholino)propoxy | amino
39 | 3-(4-morpholino)propoxy | 4-morpholino
40 | 3-(4-morpholino)propoxy | 1-piperidino

TABLE 4

No. | R² | R³ | R⁵ | R⁶ | R⁷
--- | --- | --- | --- | --- | ---
41 | OCH₃ | OCH₃ | OCH₂-(2-pyridyl) | CH₃ | H
42 | OCH₃ | OCH₃ | OCH₂-(4-methyl-2-pyridyl) | CH₃ | H
43 | OCH₃ | OCH₃ | OCH₂-(4-methoxy-2-pyridyl) | CH₃ | H
44 | OCH₃ | OCH₃ | OCH₂-(6-methyl-2-pyridyl) | CH₃ | H
45 | OCH₃ | OCH₂CF₃ | OCH₂-(2-pyridyl) | F | H
46 | OCH₃ | 3-(4-morpholino)-propoxy | 4-chlorophenoxy | Cl | H
47 | OCH₃ | 3-(4-morpholino)-propoxy | (4-chlorophenyl)thio | Cl | Cl
48 | acetoxy | OCH₃ | OCH₂-(2-pyridyl) | F | H

TABLE 5

No. | R³ | Rᵃ
--- | --- | ---
49 | 3-(4-morpholino)propoxy | 3-quinolinyl

Certain compounds of formula (I) are novel and these form a further aspect of the invention. Particular examples of such compounds are compounds of formula (IIB)

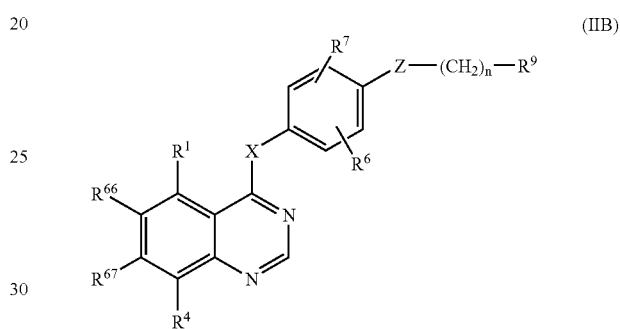

(IIB)

or a salt, ester, amide or prodrug thereof;

where X, Z, $R^1$, $R^4$, $R^9$, $R^6$ and $R^7$ and n are as defined in relation to formula (II) and $R^{66}$ is halo, cyano, nitro, trifluoromethyl, $C_{1-3}$alkyl, —$NR^{12}R^{13}$ (wherein $R^{12}$ and $R^{13}$, which may be the same or different, each represents hydrogen or $C_{1-6}$alkyl), or a group —$X^1R^{14}$ where $X^1$ and $R^{14}$ are as defined in relation to formula (I) and $R^{14}$ is particularly a group of sub group (1) or (10), and $R^{67}$ is $C_{1-6}$alkoxy optionally substituted by fluorine or a group $X^1R^{38}$ in which $X^1$ and $R^{38}$ are as defined in relation to formula (I), and in particular $X^1$ is oxygen and $R^{38}$ is or a 5–6-membered aromatic heterocyclic group (linked via nitrogen) with 1–3 heteroatoms selected from O, N and S; provided that at least one of $R^{66}$ and $R^{67}$ is other than unsubstituted methoxy.

Suitably, X, Z, $R^1$, $R^4$, $R^9$, $R^6$ and $R^7$ and n are as defined in relation to formula (IIA) and $R^{66}$ is halo, cyano, nitro, trifluoromethyl, $C_{1-3}$alkyl, —$NR^{12}R^{13}$ (wherein $R^{12}$ and $R^{13}$, which may be the same or different, each represents hydrogen or $C_{1-3}$alkyl), or a group —$X^1R^{14}$ where $X^1$ and $R^{14}$ are as defined in relation to formula (I) and $R^{14}$ is particularly a group of sub group (1') or (10'), and $R^{67}$ is $C_{1-6}$alkoxy optionally substituted by fluorine or a group $X^1R^{38}$ in which $X^1$ and $R^{38}$ are as defined in relation to formula (IIA).

A preferred example of $R^{67}$ is 3-morpholinopropoxy.

Preferably $X^1$ is oxygen.

Preferably at least $R^{67}$ is other than unsubstituted alkoxy.

Where $R^{66}$ or $R^{67}$ is unsubstituted alkoxy, it is preferably methoxy.

Suitable halo substitutents for $R^{66}$ and $R^{67}$ are fluoro.

Other examples for $R^{66}$ and/or $R^{67}$ include 3,3,3-trifluoroethoxy.

Other novel compounds of formula (I) which form a further aspect of the invention are compounds of formula (IIIB)

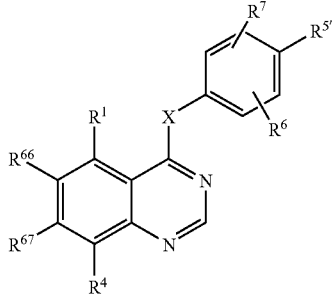

(IIIB)

or a salt, ester, amide or prodrug thereof;

where X, $R^4$, $R^1$, $R^6$ and $R^7$ are as defined in relation to formula (III) and $R^{66}$ are $R^{67}$ are as defined in relation to formula (IIB) and $R^{5'}$ is as defined in relation to formula (III).

Suitably X, $R^4$, $R^1$, $R^6$ and $R^7$ are as defined in relation to formula (IIIA), $R^{66}$ are $R^{67}$ are as defined in relation to formula (IIB) and $R^{5'}$ is as defined in relation to formula (IIIA).

Preferred subgroups of $R^{66}$ and $R^{67}$ are as set out in relation to formula (IIA).

Yet further novel compounds of the invention are compounds of formula (IVB)

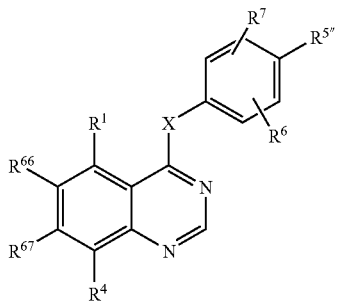

or a salt, ester, amide or prodrug thereof;

where X, $R^1$, $R^4$, $R^6$ and $R^7$ are as defined in relation to formula (I), $R^{5''}$ is as defined in relation to formula (IV) and $R^{66}$ are $R^{67}$ are as defined in relation to formula (IIB).

Suitably, X, $R^1$, $R^4$, $R^6$ and $R^7$ are as defined in relation to formula (IVA), and $R^{5''}$ is as defined in relation to formula (IVA).

Preferred subgroups of $R^{66}$ and $R^{67}$ are as set out in relation to formula (IIB).

Other examples of novel compounds include compounds of formula (IVC)

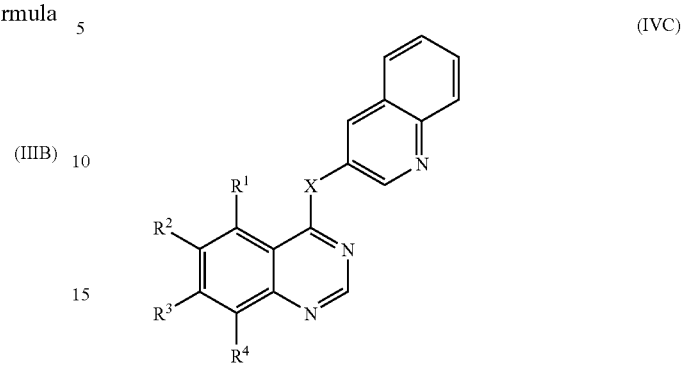

(IVC)

or a salt, ester, amide or prodrug thereof;

where $R^1$, $R^2$, $R^3$, $R^4$ and X are as defined in relation to formula (I) and in particular are as defined in relation to formula (IVA).

Compounds of formula (I) may be prepared by methods known in the art or by analogous methods. For example, a compound of formula (I) can be prepared by reacting a compound of formula (VII)

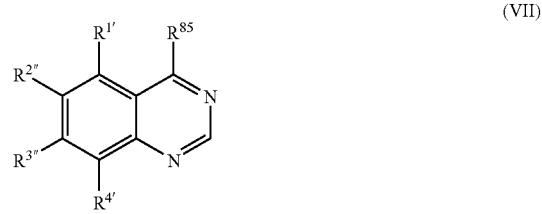

(VII)

where $R^{1'}$, $R^{2''}$, $R^{3'''}$, and $R^{4'}$ are equivalent to a group $R^1$, $R^2$, $R^3$ and $R^4$ as defined in relation to formula (I) or a precursor thereof, and $R^{85}$ is a leaving group, with a compound of formula (VIII)

$$H-X-R^a \qquad (VIII)$$

where X, and $R^a$ are as defined in relation to formula (I), and thereafter if desired or necessary converting a group $R^{1'}$, $R^{2''}$, $R^{3'''}$ or $R^{4'}$ to a group $R^1$, $R^2$, $R^3$ and $R^4$ respectively or to a different such group.

Suitable leaving groups for $R^{85}$ include halo such as chloro, mesylate and tosylate. The reaction is suitably effected in an organic solvent such as an alcohol like isopropanol, at elevated temperatures, conveniently at the reflux temperature of the solvent.

The conversion of a group $R^{1'}$, $R^{2''}$, $R^{3'''}$ or $R^{4'}$ to a group $R^1$, $R^2$, $R^3$ and $R^4$ respectively or to a different such group, may be particularly useful in connection with the preparation of compounds of formula (IIB), (IIIB) and (IVB) and examples of these preparations are provided hereinafter.

The use of this method in the preparation of novel compounds such as (IIB), (IIIB), (IVB) and (IVC) forms a further aspect of the invention.

Compounds of formula (VII) and (VIII) are either known compounds or they can be derived from known compounds by conventional methods. Examples of compounds of formula (VIII) include compounds of formula (IX), (X) or (XI)

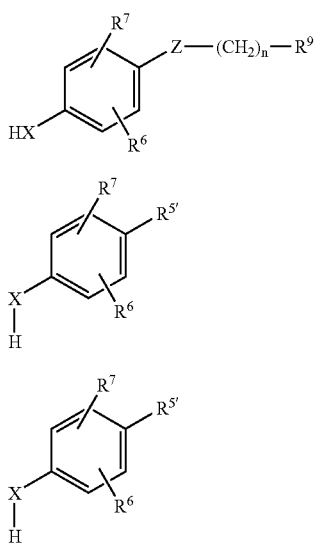

where X, $R^6$, $R^7$, Z, n, $R^9$ are as defined in relation to formula (I), $R^{5'}$ is as defined in relation to formula (II) and $R^{5''}$ is as defined in relation to formula (IV).

Compounds of formula (I) are inhibitors of aurora 2 kinase. As a result, these compounds can be used to treat disease mediated by these agents, in particular proliferative disease.

According to a further aspect of the present invention there is provided a method for inhibiting aurora 2 kinase in a warm blooded animal, such as man, in need of such treatment, which comprises administering to said animal an effective amount of a compound of formula (I), or a salt, ester, amide or prodrug thereof, and suitably a pharmaceutically acceptable salt, or an in vivo hydrolysable ester thereof.

Novel compounds of formula (I) have not hitherto been proposed for use in therapy. Thus, according to a further aspect of the invention there is provided a compound of the formula (IIB), (IIIB), (IVB) or (IVC) as defined herein, or a pharmaceutically acceptable salt or an in vivo hydrolysable ester thereof, for use in a method of treatment of the human or animal body by therapy. In particular, the compounds are used in methods of treatment of proliferative disease such as cancer and in particular cancers such as colorectal or breast cancer where aurora 2 is upregulated.

Compounds of formula (I) are suitably applied in the form of a pharmaceutical composition. Preferred compounds of formula (I) for use in the compositions of the invention are as described above.

Some of these are novel and form yet a further aspect of the invention. Thus, the invention also provides a pharmaceutical composition comprising a compound of formula (IIB), (IIIB), (IVB) or (IVC) as defined herein, or a pharmaceutically acceptable salt, or an in vivo hydrolysable ester thereof, in combination with at pharmaceutically acceptable carrier.

The compositions of compounds of formula (I) may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 µl or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of aurora 2 kinase.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated $DMSOd_6$ (unless otherwise stated) on the delta scale (ppm downfield from tetramethylsilane) using a Varian Gemini 2000 spectrometer operating at a field strength of 300 MHz, or a Bruker DPX300 spectrometer operating at a field strength of 300 MHz; and peak multiplicities are shown as follows: s, singlet; d, doublet; dd, double doublet; t, triplet; q, quartet; qu, quintet; m, multiplet; bs, broad singlet; mass spectrometry (MS) was performed by electrospray on a VG platform;

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Savant AES 2000; column chromatography was performed using either an Anachem Sympur MPLC or Jones Flashmaster MPLC systems on silica using Varian Mega Bond Elut cartridges; the structures of the final products were confirmed by LCMS on a Micromass OpenLynx system using the following and are quoted as retention time (RT) in minutes:

| Column: | 4.6 mm × 3 cm Hichrom RPB |
|---|---|
| Solvent A: | 5% Methanol in Water + 0.1% formic acid |
| Solvent B: | 5% Methanol in Acetonitrile + 0.1% formic acid |
| Flow rate: | 1.4 ml/min |
| Run time: | 5 minutes with a 4.5 minute gradient from 0–100% B |
| Wavelength: | 254 nm, bandwidth 10 nm |
| Mass detector: | Micromass Platform LC |
| Injection volume | 0.002 ml |

(viii) intermediates were not generally fully characterised and purity was assessed by thin layer chromatography (TLC), HPLC, infra-red (IR), MS or NMR analysis;

EXAMPLE 1

Preparation of Compound No. 1 in Table 1

4-Chloro-6,7-dimethoxyquinazoline (112 mg, 0.50 mmol) and potassium carbonate (69 mg, 0.50 mmol) were added sequentially to a stirred suspension of 4-n-propoxyphenol (76 mg, 0.50 mmol) in dimethylformamide (3 ml). The reaction was heated at 100° C. for 4 hours then allowed to stir for a further 36 hours at ambient temperature. Brine (10 ml) was added and the reaction allowed to stand for 16 hours before the solid was collected by suction filtration (analogous reactions which failed to yield a solid precipitate were extracted with dichloromethane (2×5 ml) and the dichloromethane layer evaporated in vacuo to give a solid product). Drying in vacuo yielded the title compound (66.3 mg, 56% yield) as a white solid:
$^1$H-NMR (DMSO $d_6$): 8.55 (s, 1H), 7.57 (s, 1H), 7.39 (s, 1H), 7.22 (d, 2H), 7.03 (d, 2H), 4.00 (s, 3H), 3.98 (s, 3H), 3.97 (t, 2H), 1.70–1.82 (m, 2H), 1.02 (t, 3H):
MS (+ve ESI): 341 (M+H)$^+$.

4-Chloro-6,7-dimethoxyquinazoline, used as the starting material was obtained as follows:

a) A mixture of 4,5-dimethoxyanthranilic acid (19.7 g, 100 mmol) and formamide (10 ml) was heated at 190° C. for 5 hours. The mixture was allowed to cool to approximately 80° C. and water (50 ml) was added. The mixture was then allowed to stand at ambient temperature for 3 hours. Collection of the solid by suction filtration, followed by washing with water (2×50 ml) and drying in vacuo, yielded 6,7-dimethoxy-3,4-dihydroquinazolin-4-one (3.65 g, 18% yield) as a white solid.
$^1$H-NMR (DMSO $d_6$): 12.10 (s, 1H), 7.95 (s, 1H), 7.42 (s, 1H), 7.11 (s, 1H), 3.88 (s, 3H), 3.84 (s, 3H):
MS (–ve ESI): 205 (M–H)$^-$.

b) Dimethylformamide (0.2 ml) was added dropwise to a solution of 6,7-dimethoxy-3,4-dihydro-quinazolin-4-one (10.0 g, 48.5 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6,7-dimethoxyquinazoline (10.7 g, 98% yield) as a white solid:
$^1$H-NMR (DMSO $d_6$): 8.86 (s, 1H), 7.42 (s, 1H), 7.37 (s, 1H), 4.00 (s, 3H), 3.98 (s, 3H):
MS (+ve ESI): 225 (M–H)$^+$.

EXAMPLE 2

Preparation of Compound No. 2 in Table 1

An analogous reaction to that described in example 1, but starting with 4-phenoxyphenol (85 mg, 0.50 mmol) yielded the title compound (165 mg, 84% yield) as a white solid:
$^1$H-NMR (DMSO $d_6$): 8.59 (s, 1H), 7.58 (s, 1H), 7.44 (t, 2H), 7.40 (s, 1H), 7.36 (d, 2H), 7.18 (t, 1H), 7.11 (d, 2H), 7.07 (d, 2H), 4.00 (s, 3H), 3.99 (s, 3H):
MS (+ve ESI): 375 (M+H)$^+$.

EXAMPLE 3

Preparation of Compound No. 3 in Table 1

An analogous reaction to that described in example 1, but starting with 4-benzyloxyphenol (100 mg, 0.50 mmol) yielded the title compound (182 mg, 94% yield) as a white solid:
$^1$H-NMR (DMSO $d_6$): 8.54 (s, 1H), 7.57 (s, 1H), 7.50 (d, 2H), 7.43 (t, 2H), 7.40 (s, 1H), 7.35 (t, 1H), 7.25 (d, 2H), 7.11 (d, 2H), 5.16 (s, 2H), 3.99 (s, 3H), 3.98 (s, 3H):
MS (–ve ESI): 387 (M–H)$^-$.

EXAMPLE 4

Preparation of Compound No. 4 in Table 1

An analogous reaction to that described in example 1, but starting with 4-(methylmercapto)phenol (70 mg, 0.50 mmol) yielded the title compound (146 mg, 89% yield) as a white solid:
$^1$H-NMR (DMSO $d_6$): 8.55 (s, 1H), 7.56 (s, 1H), 7.36–7.42 (m, 3H), 7.29 (d, 2H), 3.99 (s, 3H), 3.98 (s, 3H), 2.53 (s, 3H):
MS (+ve ESI): 329 (M+H)$^+$.

EXAMPLE 5

Preparation of Compound No. 5 in Table 1

An analogous reaction to that described in example 1, but starting with 4-pentyloxyphenol (90 mg, 0.50 mmol) yielded the title compound (166 mg, 90% yield) as a white solid:
$^1$H-NMR (DMSO $d_6$): 8.54 (s, 1H), 7.56 (s, 1H), 7.38 (s, 1H), 7.21 (d, 2H), 7.02 (d, 2H), 4.01 (t, 2H), 4.00 (s, 3H), 3.99 (s, 3H), 1.71–1.81 (m, 2H), 1.32–1.49 (m, 4H), 0.92 (t, 3H):
MS (+ve ESI): 369 (M+H)$^+$.

EXAMPLE 6

Preparation of Compound No. 6 in Table 1

An analogous reaction to that described in example 1, but starting with methyl 3-(4-hydroxyphenyl)-propionate (90 mg, 0.50 mmol) yielded the title compound (135 mg, 73% yield) as a white solid:

$^1$H-NMR (DMSO d$_6$): 8.56 (s, 1H), 7.57 (s, 1H), 7.40 (s, 1H), 7.35 (d, 2H), 7.23 (d, 2H), 4.00 (s, 3H), 3.98 (s, 3H), 3.62 (s, 3H), 2.90 (t, 2H), 2.70 (t, 2H):

MS (+ve ESI): 369 (M+H)$^+$.

EXAMPLE 7

Preparation of Compound No. 7 in Table 1

An analogous reaction to that described in example 1, but starting with 4-hydroxy-4'-nitrobiphenyl (108 mg, 0.50 mmol) yielded the title compound (188 mg, 93% yield) as a white solid:

$^1$H-NMR (DMSO d$_6$): 8.58 (s, 1H), 8.33 (d, 2H), 8.02 (d, 2H), 7.92 (d, 2H), 7.59 (s, 1H), 7.49 (d, 2H), 7.40 (s, 1H), 4.00 (s, 3H), 3.99 (s, 1H):

MS (+ve ESI): 404 (M+H)$^+$.

EXAMPLE 8

Preparation of Compound No. 8 in Table 1

An analogous reaction to that described in example 1, but starting with 4-phenylphenol (85 mg, 0.50 mmol) yielded the title compound (170 mg, 95% yield) as a white solid:

$^1$H-NMR (DMSO d$_6$): 8.60 (s, 1H), 7.79 (d, 2H), 7.73 (d, 2H), 7.61 (s, 1H), 7.47–7.55 (m, 2H), 7.37–7.46 (m, 4H), 4.00 (s, 6H):

MS (+ve ESI): 359 (M+H)$^+$.

EXAMPLE 9

Preparation of Compound No. 9 in Table 1

An analogous reaction to that described in example 1 but starting with 4-n-propylphenol (68 mg, 0.50 mmol) yielded the title compound (87 mg, 54% yield) as a white solid:

$^1$H-NMR (DMSO d$_6$): 8.55 (s, 1H), 7.57 (s, 1H), 7.39 (s, 1H), 7.30 (d, 2H), 7.21 (d, 2H), 4.00 (s, 3H), 3.98 (s, 3H), 2.61 (t, 2H), 1.58–1.72 (m, 2H), 0.94 (t, 3H):

MS (+ve ESI): 325 (M+H)$^+$.

EXAMPLE 10

Preparation of Compound No. 10 in Table 1

An analogous reaction to that described in example 1, but starting with 4-hydroxydiphenylmethane (92 mg, 0.50 mmol) yielded the title compound (44 mg, 24% yield) as a white solid:

$^1$H-NMR (DMSO d$_6$): 8.53 (s, 1H), 7.55 (s, 1H), 7.38 (s, 1H), 7.28–7.37 (m, 7H), 7.23 (d, 2H), 4.01 (s, 2H), 4.00 (s, 3H), 3.98 (s, 3H):

MS (+ve ESI): 373 (M+H)$^+$.

EXAMPLE 11

Preparation of Compound No. 11 in Table 1

An analogous reaction to that described in example 1, but starting with 4-bromo-4'-hydroxybiphenyl (125 mg, 0.50 mmol) yielded the title compound (205 mg, 94% yield) as a white solid:

$^1$H-NMR (DMSO d$_6$): 8.59 (s, 1H), 7.79 (d, 2H), 7.69 (s, 4H), 7.60 (s, 1H), 7.42 (d, 2H), 7.40 (s, 1H), 4.01 (s, 3H), 4.00 (s, 3H):

MS (+ve ESI): 437 (M+H)$^+$.

EXAMPLE 12

Preparation of Compound No 12 in Table 1

An analogous reaction to that described in example 1, but starting with 3-(4-hydroxyphenyl)propionitrile (73 mg, 0.50 mmol) yielded the title compound (150 mg, 89% yield) as a white solid:

$^1$H-NMR (DMSO d$_6$): 8.57 (s, 1H), 7.57 (s, 1H), 7.41 (d, 2H), 7.39 (s, 1H), 7.28 (d, 2H), 4.00 (s, 3H), 3.99 (s, 3H), 2.82–3.00 (m, 4H):

MS (+ve ESI): 336 (M+H)$^+$.

EXAMPLE 13

Preparation of Compound No. 13 in Table 1

An analogous reaction to that described in example 1, but starting with 4-iodophenol (244 mg, 1.10 mmol) yielded the title compound (340 mg, 83% yield) as a white solid:

$^1$H-NMR (DMSO d$_6$): 8.55 (s, 1H), 7.80 (d, 2H, J=8 Hz), 7.50 (s, 1H), 7.35 (s, 1H), 7.15 (d, 2H, J=8 Hz), 3.95 (s, 3H), 3.90 (s, 3H):

MS (+ve ESI): 409 (M−H)$^+$.

EXAMPLE 14

Preparation of Compound No. 14 in Table 1

An analogous reaction to that described in example 1, but starting with 4-phenylazophenol (99 mg, 0.50 mmol) yielded the title compound (177 mg, 92% yield) as a white solid:

$^1$H-NMR (DMSO d$_6$): 8.60 (s, 1H), 8.05 (d, 2H), 7.94 (d, 2H), 7.54–7.68 (m, 6H), 7.42 (s, 1H), 4.01 (s, 6H):

MS (+ve ESI): 385 (M+H)$^+$.

EXAMPLE 15

Preparation of Compound No. 15 in Table 2

An analogous reaction to that described in example 1, but starting with 3,4-difluorophenol (65 mg, 0.50 mmol) yielded the title compound (135 mg, 85% yield) as a white solid:

$^1$H-NMR (DMSO d$_6$): 8.59 (s, 1H), 7.53–7.67 (m, 2H), 7.57 (s, 1H), 7.40 (s, 1H), 7.22–7.29 (m, 1H), 4.00 (s, 3H), 3.98 (s, 3H):

MS (+ve ESI): 319 (M+H)$^+$.

EXAMPLE 16

Preparation of Compound No. 16 in Table 2

An analogous reaction to that described in example 1, but starting with 5-chloro-2-hydroxybiphenyl (102 mg, 0.50 mmol) yielded the title compound (184 mg, 94% yield) as a white solid:

¹H-NMR (DMSO d₆): 8.46 (s, 1H), 7.49–7.63 (m, 5H), 7.48 (s, 1H), 7.30 (s, 1H), 7.29 (m, 3H, 3.97 (s, 6H):

MS (+ve ESI): 393 (M+H)⁺.

EXAMPLE 17

Preparation of Compound No. 17 in Table 3

A solution of 4-n-butoxyaniline (110 mg, 0.67 mmol) in isopropanol (7 ml) was added to 4-chloro-6,7-dimethoxyquinazoline hydrochloride (174 mg, 0.67 mmol) and the reaction heated at 73° C. for 2 hours before being cooled to 5° C. The solid which precipitated was collected by suction filtration and washed with diethyl ether (2×5 ml). Drying of this material in vacuo yielded the title compound (80 mg, 34% yield) as an off-white solid:

¹H-NMR (DMSO d₆): 11.25 (s, 1H), 8.74 (s, 1H,), 8.24 (s, 1H), 7.54 (d, 2H, J=8 Hz), 7.31 (s, 1H), 7.01 (d, 2H, J=8 Hz), 3.99 (m, 2H), 3.99 (s, 3H), 3.97 (s, 3H), 1.70 (m, 2H), 1.45 (m, 2H), 0.93 (t, 3H, J=7 Hz):

MS (−ve ESI): 352 (M−H)⁻,

MS (+ve ESI): 354 (M+H)⁺.

EXAMPLE 18

Preparation of Compound No. 18 in Table 3

A mixture of 4-(4-hydroxyanilino)-6,7-dimethoxyquinazoline hydrochloride (100 mg, 0.30 mmol), potassium carbonate (137 mg, 0.99 mmol) and 2-picolyl chloride hydrochloride (54 mg, 0.33 mmol) were heated in dimethylformamide (5 ml) at 100° C. for 4 hours and then allowed to cool to ambient temperature. The reaction was poured into water (50 ml) and the aqueous phase was extracted with dichloromethane (3×50 ml). The combined organic layers were evaporated in vacuo to a volume of 10 ml, and then diethyl ether was added (25 ml) to cause precipitation of a brown solid, which was collected by suction filtration. Purification by chromatography on a silica gel bond-elute cartridge, eluting with 4% methanol in dichloromethane yielded the title compound (48 mg, 41% yield) as a white solid:

¹H-NMR (DMSO d₆): 9.36 (s, 1H), 8.58 (d, 1H, J=8 Hz), 8.36 (s, 1H), 7.79–7.85 (m, 1H), 7.79 (s, 1H), 7.61 (d, 2H, J=8 Hz), 7.52 (d, 1H, J=8 Hz), 7.31–7.35 (m, 1H), 7.14 (s, 1H), 7.04 (d, 2H, J=8 Hz), 5.19 (s, 2H), 3.94 (s, 3H), 3.88 (s, 3H):

MS (−ve ESI): 236 (M−H)⁻,

MS (+ve ESI): 238 (M+H)⁺.

4-(4-Hydroxyanilino)-6,7-dimethoxyquinazoline hydrochloride, used as the starting material was obtained as follows:

An analogous reaction to that described in example 17, but starting with 4aminophenol (530 mg, 4.90 mmol), 4-(4-Hydroxyanilino)-6,7-dimethoxyquinazoline hydrochloride (1.34 g, 90% yield) as a white solid:

¹H-NMR (DMSO d₆): 11.24 (s, 1H), 9.66 (s, 1H), 8.72 (s, 1H), 8.24 (s, 1H), 7.40 (d, 2H, =8 Hz), 7.34 (s, 1H), 6.84 (d, 2H, J=8 Hz), 3.96 (s, 3H), 3.94 (s, 3H):

MS (−ve ESI): 296 (M−H)⁻,

MS (+ve ESI): 298 (M+H)⁺.

EXAMPLE 19

Preparation of Compound No. 19 in Table 3

An analogous reaction to that described in example 18, but starting with phenethyl bromide (90.8 mg, 0.40 mmol), potassium carbonate (96 mg, 0.69 mmol) and 4-(4-hydroxyanilino)-6,7-dimethoxyquinazoline hydrochloride (105 mg, 0.31 mmol), yielded the title compound (41 mg, 33% yield) as a pale yellow solid, after purification by chromatography on silica gel, eluting with 2% methanol in dichloromethane:

¹H-NMR (DMSO d₆): 8.61 (s, 1H), 7.51 (d, 2H, J=8 Hz), 7.23–7.35 (m, 6H), 7.05 (s, 1H), 6.99 (s, 1H), 6.94 (d, 2H, J=8 Hz), 4.20 (t, 2H, J=8 Hz), 4.01 (s, 3H), 3.98 (s, 3H), 3.11 (t, 2H, J=8 Hz):

MS (−ve ESI): 400 (M−H)⁻,

MS (+ve ESI): 402 (M+H)⁺.

EXAMPLE 20

Preparation of Compound No. 20 in Table 3

An analogous reaction to that described in example 18, but starting with allyl bromide (0.055 ml, 0.64 mmol), potassium carbonate (96 mg, 0.69 mmol) and 4-(4-hydroxyanilino)-6,7-dimethoxyquinazoline hydrochloride (105 mg, 0.31 mmol), yielded the title compound (42 mg, 39% yield) as a pale yellow solid, after purification by chromatography on silica gel, eluting with 2% methanol in dichloromethane:

¹H-NMR (DMSO d₆): 8.61 (s, 1H), 7.51 (d, 2H, J=8 Hz), 7.24 (s, 1H), 7.12 (s, 1H), 7.01 (s, 1H), 6.96 (d, 2H, J=8 Hz), 6.00–6.14 (m, 1H), 5.43 (dd, 1H, J=2,16 Hz), 5.28 (dd, 1H, J=2,10 Hz), 4.54 (d, 2H, J=7 Hz), 4.00 (s, 3H), 3.96 (s, 3H):

MS (−ve ESI): 336 (M−H)⁻,

MS (+ve ESI): 338 (M+H)⁺.

EXAMPLE 21

Preparation of Compound No. 21 in Table 3

Triethylamine (0.10 ml, 0.72 mmol), tributylphosphine (0.45 ml, 1.83 mmol) and furfuyl alcohol (0.106 ml, 1.22 mmol) were added to a suspension of 4-(4-hydroxyanilino)-6,7-dimethoxyquinazoline hydrochloride (205 mg, 0.61 mmol) in dichloromethane (20 ml) at ambient temperature. The reaction was stirred for 20 minutes before addition of 1,1'-(azodicarbonyl)dipiperidine (462 mg, 1.83 mmol) and then stirred for a further 3 hours. Tributylphosphine (0.45 ml, 1.83 mmol) and 1,1-(azodicarbonyl)dipiperidine (462 mg, 1.83 mmol) were added and the reaction stirred for 2 hours at ambient temperature. The reaction mixture was transferred to an SCX column which was eluted with 0–5% methanol in dichloromethane before the product was eluted with 3% ammonium hydroxide/20% methanol in dichloromethane. Evaporation of the desired fractions in vacuo, followed by trituration of the solid product with ethyl acetate, yielded the title compound (34 mg, 15% yield) as a white solid, after drying in vacuo:

¹H-NMR (DMSO d₆): 9.38 (s, 1H), 8.39 (s, 1H), 7.81 (s, 1H), 7.69 (s, 1H), 7.63 (d, 1H, J=8 Hz), 7.16 (s, 1H), 7.05 (d, 2H, J=8 Hz), 6.58 (d, 1H, J=5 Hz), 6.46 (d, 2H, J=5 Hz), 5.07 (s, 2H), 3.96 (s, 3H), 3.93 (s, 3H):

MS (−ve ESI): 376 (M−H)⁻,

MS (+ve ESI): 378 (M+H)⁺.

EXAMPLE 22

Preparation of Compound No. 22 in Table 3

Bis(triphenylphosphine) palladium (II) chloride (570 mg, 0.81 mmol) was added to a mixture of triethylamine (2.38 ml, 41.2 mmol), 4-(4-iodoanilino)-6,7-dimethoxyquinazoline (3.00 g, 6.77 mmol), copper (1) iodide (154 mg, 0.81 mmol) and (trimethylsilyl)acetylene (2.66 ml, 20.3 mmol) in tetrahydrofuran (60 ml) under an inert atmosphere and the reaction was stirred for 48 hours at ambient temperature. The solvents were removed in vacuo, the reaction was partitioned between ethyl acetate (50 ml) and water (50 ml) and the biphasic mixture was filtered through celite. The organic layer was separated, washed with brine (50 ml), dried over magnesium sulphate and evaporated in vacuo. Purification by flash chromatography on silica gel, eluting with 50–100% ethyl acetate in isohexane, yielded the title compound (1.95 g, 77% yield) as a yellow solid:

$^1$H-NMR (DMSO d$_6$): 9.30 (s, 1H), 8.31 (s, 1H), 7.70 (d, 2H), 7.60 (s, 1H), 7.25 (d, 2H), 7.01 (s, 1H), 3.75 (s, 3H), 3.70 (s, 3H), 0.00 (s, 9H):

MS (−ve ESI): 376 (M−H)$^−$,
MS (+ve ESI): 378 (M+H)$^+$.

4-(4-iodoanilino)-6,7-dimethoxyquinazoline, used as the starting material was obtained as follows:

An analogous reaction to that described in example 17, but starting with 4-iodoaniline (4.89 g, 22.3 mmol), yielded 4-(4-iodoanilino)-6,7-dimethoxyquinazoline (9.38 g, 95% yield) as a white solid:

$^1$H-NMR (DMSO d$_6$): 11.33 (s, 1H), 8.81 (s, 1H), 8.30 (s, 1H), 7.80 (s, 1H), 7.55 (d, 2H), 7.30 (s, 1H), 4.02 (s, 3H), 3.93 (s, 3H):

MS (−ve ESI): 406 (M−H)$^−$; MS (+ve ESI): 408 (M+H)$^+$.

EXAMPLE 23

Preparation of Compound No. 23 in Table 3

Tetrabutylammonium flouride (5.84 ml of a 1.0N solution in tetrahydrofuran, 5.84 mmol) was added to a solution of 4-(4-(2-(trimethylsily)ethynyl)anilino)-6,7-dimethoxyquinazoline (1.83 g, 4.85 mmol) in tetrahydrofuran (150 ml) at 10° C. under an inert atmosphere and the reaction allowed to stir for 10 minutes at 10° C. before the reaction was poured into brine (100 ml). The reaction was extrcated with ethyl acetate (3×50 ml), the combined organic layers were washed with saturated aqueous sodium bicarbonate solution (100 ml), dried over magnesium sulphate and evaporated in vacuo. Purification by flash chromatography on silica gel, eluting with i) 50–100% ethyl acetate in isohexane ii) 10% methanol in ethyl acetate, yielded the title compound (0.54 g, 36% yield) as a yellow solid:

$^1$H-NMR (DMSO d$_6$): 9.55 (s, 1H), 8.51 (s, 1H), 7.90 (d, 2H), 7.81 (s, 1H), 7.45 (d, 2H), 7.20 (s, 1H), 4.05 (s, 1H), 4.00 (s, 3H), 3.95 (s, 3H):

MS (−ve ESI): 304 (M−H)—,
MS (+ve ESI): 306 (M+H)$^+$.

EXAMPLE 24

Preparation of Compound No. 24 in Table 3

A mixture of ethyl 2-(4-aminophenyl)propiolate (83 mg, 0.44 mmol) and 4-chloro-6,7-dimethoxyquinazoline (98 mg, 0.44 mmol) was heated in ethanol (8 ml) at reflux for 16 hours. The reaction was allowed to cool and the solid which precipitated was collected by suction filtration. Purification by reverse phase hplc, eluting with 35% aqueous acetonitrile (containing 0.1% trifluoroacetic acid), yielded the title compound (22 mg, 13% yield) as a white solid:

$^1$H-NMR (DMSO d$_6$): 9.65 (s, 1H), 8.55 (s, 1H), 8.00 (d, 2H), 7.85 (s, 1H), 7.70 (d, 2H), 7.20 (s, 1H), 4.20 (q, 2H), 3.99 (s, 3H), 3.57 (s, 3H), 1.25 (t, 3H):

MS (−ve ESI): 376 (M−H)$^−$,
MS (+ve ESI): 378 (M+H)$^+$.

Ethyl 2-(4-aminophenyl)propiolate, used as starting material was obtained as follows:

a) Palladium (II) bis(triphenylphosphine) dichloride (140 mg, 0.20 mmol), copper (I) iodide (76 mg, 0.40 mmol) and potassium carbonate (2.8 g, 20 mmol) were added to a solution of 4-iodo-nitrobenzene (2.49 g, 10.0 mmol) and ethyl propiolate (3.92 g, 40 mmol) in tetrahydrofuran (30 ml) and the reaction heated at reflux for 16 hours under an inert atmosphere. The reaction was cooled to ambient temperature, poured into water (150 ml), diluted with ethyl acetate (75 ml) and filtered through celite. The organic layer was separated, the aqueous was extracted with ethyl acetate (2×100 ml) and the combined organic layers were dried over magnesium sulphate before solvent evaporation in vacuo. Purification by flash chromatography on silica gel, eluting with 25% ethyl acetate in isohexane, yielded ethyl 2-(4-nitrophenyl)propiolate (1.55 g, 71% yield) as a yellow solid:

$^1$H-NMR (DMSO d$_6$): 8.25–8.30 (m, 2H), 7.90–7.95 (m, 2H), 4.25 (q, 2H, J=7 Hz), 1.25 (t, 3H):

MS (+ve ESI): 219 (M+H)$^+$.

b) Water (6 ml) and sodium hydrosulphite (1.39 g, 8.0 mmol) were added to a refluxing solution of ethyl 2-(4-nitrophenyl)propiolate (700 mg, 3.2 mmol) in ethanol (30 ml). The reaction was heated for 5 minutes and more water (6 ml) and sodium hydrosulphite (1.39 g, 8.0 mmol) were added. After a further 5 minutes, the reaction was poured into water, the aqueous layer was extracted with ethyl acetate and the combined organic layers were dried over magnesium sulphate before solvent evaporation in vacuo. Purification by flash chromatography on silica gel, eluting with 33% ethyl acetate in isohexane, yielded ethyl 2-(4-aminophenyl)propiolate (83 mg, 14% yield) as a white solid:

$^1$H-NMR (DMSO d$_6$): 7.25 (d, 2H, J=8 Hz), 6.55 (d, 2H; J=8 Hz), 5.95 (s, 2H), 4.35 (q, 2H, J=7 Hz), 1.20 (t, 3H, J=7 Hz):

MS (−ve ESI): 187.9 (M−H)$^−$,
MS (+ve ESI): 189.9 (M+H)$^+$.

EXAMPLE 25

Preparation of Compound No. 25 in Table 3

A slurry of 10% palladium on carbon (20 mg) in acetic acid (3 ml) was added to a solution of 4-(4-(2-carboethoxy)ethenyl)anilino)-6,7-dimethoxyquinazoline (200 mg, 0.53 mmol) and the reaction was stirred for 48 hours at ambient temperature under an atmosphere of hydrogen. The reaction was filtered through celite, the solvents were removed in vacuo and the residue was treated with aqueous sodium hydrogen carbonate solution (50 ml). The reaction was extracted with a mixture of ethyl acetate (25 ml) and diethyl ether (25 ml) and the combined organic layers were evaporated in vacuo to yield the title compound (1165 mg, 82% yield) as a white solid:

$^1$H-NMR (DMSO d$_6$): 9.40 (s, 1H), 8.42 (s, 1H), 7.79 (s, 1H), 7.65 (d, 2H), 7.20 (d, 2H), 7.19 s, 1H), 4.00–4.10 (m, 2H), 3.95 (s, 3H), 3.93 (s, 3H), 2.79–2.90 (m, 2H), 2.60–2.65 (m. 2H), 1.10–1.20 (m, 2H):

MS (−ve ESI): 380 (M−H)$^-$,
MS (+ve ESI): 382 (M+H)$^+$.

EXAMPLE 26

Preparation of Compound No. 26 in Table 3

A solution of 4-chloro-6,7-dimethoxyquinazoline (2.11 g, 9.38 mmol) and N-(tert-butoxycarbonyl)-1,4-phenylenediamine (1.95 g, 9.38 mmol) in isopropanol (130 ml) was heated at reflux for 2.5 hours before the reaction was allowed to cool to ambient temperature. The solid which had precipitated was collected by suction filtration, washed with diethyl ether (2×50 ml) and dried in vacuo. The solid was taken-up in a mixture of trifluoroacetic acid (15 ml) and dichloromethane (25 ml) and the resulting solution stirred for 3 hours at ambient temperature. The solvents were evaporated in vacuo, chloroform (15 ml) was added and the reaction was evaporated in vacuo. The crude product was suspended in water (70 ml), neutralised by addition of saturated aqueous sodium bicarbonate solution and the solid which precipitated was collected by suction filtration. Drying the solid in vacuo yielded the title compound (2.46 g, 88% yield) as a pale yellow solid:

$^1$H-NMR (DMSO d$_6$): 9.17 (s, 1H), 8.28 (s, 1H), 7.76 (s, 1H), 7.27 (d, 2H, J=8 Hz), 7.09 (s, 1H), 6.57 (d, 2H, J=8 Hz), 4.91 (s, 2H), 3.91 (s, 3H), 3.89 (s, 3H):

MS (−ve ESI): 295 (M−H)$^-$.

EXAMPLE 27

Preparation of Compound No. 27 in Table 3

A solution of 4-chloro-6-methoxy-7-benzyloxyquinazoline (150 mg, 0.50 mmol) and 4-phenoxyaniline (93 mg, 0.50 mmol), in isopropanol (5.0 ml) was at 40° C. for 30 minutes and then at 83° C. for 12 hours before the reaction was allowed to cool to ambient temperature. The solid which had precipitated was collected by suction filtration and washed with diethyl ether (2×10 ml). Drying of this material yielded the title compound (209 mg, 86% yield) as an off-white solid:

$^1$H-NMR (DMSO d$_6$): 11.20 (s, 1H), 8.77 (s, 1H), 8.23 (s, 1H), 7.67 (d, 2H), 7.50 (d, 2H), 7.40–7.45 (m, 6H), 7.15 (d, 1H), 7.01–7.10 (m, 4H), 5.34 (s, 2H), 4.0 (s, 3H):

MS (+ve ESI): 450 (M+H)$^+$.

4-Chloro-6-methoxy-7-benzyloxyquinazoline, used as the starting material, was obtained as follows:

a) A mixture of 2-amino-4-benzyloxy-5-methoxybenzamide (10 g, 0.04 mol), (prepared according to *J Med. Chem.* 1977, 20, 146–149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid yielded 7-benzyloxy-6-methoxy-3,4-dihydroquinazolin-4-one (8.7 g, 84% yield) as a white solid:

b) Dimethylformamide (0.2 ml) was added dropwise to a solution of 6-methoxy-7-benzyloxy-3,4-dihydroquinazolin-4-one (5.00 g, 17.9 mmol) in thionyl chloride (100 ml) and the reaction was heated at reflux for 1 hour. The reaction was cooled, excess thionyl chloride was removed in vacuo and the residue was azeotroped with toluene (3×50 ml) to remove the last of the thionyl chloride. The residue was taken up in dichloromethane (550 ml), the solution was washed with saturated aqueous sodium hydrogen carbonate solution (100 ml) and water (100 ml) and the organic phase was dried over magnesium sulphate. Solvent evaporation in vacuo yielded 4-chloro-6-methoxy-7-benzyloxyquinazoline (4.80 g, 90% yield) as a pale brown solid:

$^1$H-NMR (DMSO d$_6$): 8.85 (s, 1H), 7.58 (s, 1H), 7.50 (d, 2H), 7.40 (m, 4H), 5.35 (s, 2H), 4.00 (s, 3H):

MS (+ve ESI): 301 (M+H)$^+$.

EXAMPLE 28

Preparation of Compound No. 28 in Table 3

An analogous reaction to that described in example 17, but starting with 4-aminothioanisole (33 mg, 0.24 mmol), yielded the title compound (103 mg, 95% yield) as a white solid:

$^1$H-NMR (DMSO d$_6$): 8.77 (s, 1H), 8.30 (s, 1H), 7.65 (d, 2H), 7.32–7.40 (m, 3H), 4.30 (t, 2H), 4.01 (s, 3H), 3.72–4.01 (m, 4H), 3.00–3.54 (m, 6H), 2.54 (s, 3H), 2.22–2.38 (m, 2H):

MS (+ve ESI): 441 (M+H)$^+$.

EXAMPLE 29

Preparation of Compound No. 29 in Table 3

An analogous reaction to that described in example 17, but starting with 4-benzyloxyaniline hydrochloride (118 mg, 0.50 mmol) and 4-chloro-6-methoxy-7-(3-morpholinopropoxy)quinazoline (168 g, 0.50 mmol), yielded the title compound (216 mg, 86% yield) as a white solid:

$^1$H-NMR (DMSO d$_6$): 9.80 (s, 1H), 8.30 (s, 1H), 7.70 (d, 2H), 7.40 (t, 2H), 7.35 (s, 1H), 7.15 (t, 1H), 7.10 (d, 2H), 7.05 (d, 2H), 4.30 (t, 2H), 4.00 (s, 3H), 3.95 (m, 2H), 3.80 (m, 2H), 3.50 (m, 2H), 3.30 (m, 2H), 3.10 (m, 2H), 2.30 (m, 2H):

MS (+ve ESI): 464 (M+H)$^+$.

EXAMPLE 30

Preparation of Compound No. 30 in Table 3

A solution of 1.0N hydrochloric acid in ether (0.50 ml, 0.50 mmol) was added to a solution of 4-benzyloxyaniline hydrochloride (118 mg, 0.50 mmol) and 4-chloro-6-methoxy-7-(3-morpholinopropoxy)quinazoline (168 mg, 0.50 mmol), in isopropanol (5.0 ml). The reaction was heated at 40° C. for 30 minutes and then at 83° C. for 12 hours. The reaction was allowed to cool to ambient temperature and the solid which had precipitated was collected by suction filtration and washed with diethyl ether (2×10 ml). Drying of this material yielded the title compound (228 mg, 85% yield) as a white solid:

$^1$H-NMR (DMSO d$_6$): 15.00 (s, 1H), 11.34 (s, 1H), 11.12 (s, 1H), 8.75 (s, 1H), 8.33 (s, 1H), 7.59 (d, 2H), 7.30–7.52 (m, 6H), 7.12 (d, 2H), 5.16 (s, 1H), 4.30 (t, 2H), 4.01 (s, 3H), 3.73–4.01 (m, 4H), 2.92–3.58 (m, 6H), 2.21–2.39 (m, 2H):

MS (+ve ESI): 501 (M+H)$^+$.

EXAMPLE 31

Preparation of Compound No. 31 in Table 3

An analogous reaction to that described in example 30, but starting with 4-amino-4'-nitrodiphenylsulphide (123 mg, 0.50 mmol) yielded the title compound (281 mg, 96% yield) as a white solid:

$^1$H-NMR (DMSO d$_6$): 11.50 (s, 1H), 11.10 (s, 1H), 8.85 (s, 1H), 8.48 (s, 1H), 8.17 (d, 2H), 8.00 (d, 2H), 7.70 (d, 2H), 7.50 (s, 1H), 7.35 (d, 2H), 4.32 (t, 2H), 4.05 (s, 3H), 3.99 (m, 2H), 3.85 (m, 2H), 3.50 (m, 2H), 3.30 (m, 2H), 3.10 (m, 2H), 2.32 (m, 2H):

MS (+ve ESI): 548 (M+H)$^+$.

EXAMPLE 32

Preparation of Compound No. 32 in Table 3

An analogous reaction to that described in example 30, but starting with 4-butoxyaniline (82 mg, 0.50 mmol) yielded the title compound (237 mg, 94% yield) as a white solid:

$^1$H-NMR (DMSO d$_6$): 11.35 (s, 1H), 11.12 (s, 1H), 8.75 (s, 1H), 8.35 (s, 1H), 7.60 (d, 2H), 7.40 (s, 1H), 7.05 (d, 2H), 4.31 (t, 2H), 4.03 (m, 2H), 4.02 (s, 3H), 3.99 (m, 2H), 3.85 (m, 2H), 3.50 (m, 2H), 3.30 (m, 2H), 3.10 (m, 2H), 2.35 (m, 2H), 1.70 (m, 2H), 1.58 (m, 2H), 0.95 (t, 3H):

MS (+ve ESI): 467 (M+H)$^+$.

EXAMPLE 33

Preparation of Compound No. 33 in Table 3

An analogous reaction to that described in example 30 but starting with 4-amino-4'-chlorodiphenyl ether (110 mg, 0.50 mmol) yielded the title compound (244 mg, 88% yield) as a white solid:

$^1$H-NMR (DMSO d$_6$): 11.50 (s, 1H), 11.10 (s, 1H), 8.80 (s, 1H), 8.40 (s, 1H), 7.75 (d, 2H), 7.47 (d, 2H), 7.40 (s, 1H), 7.15 (d, 2H), 7.08 (d, 2H), 4.35 (t, 2H), 4.03 (s, 3H), 3.95 (m, 2H), 3.85 (m, 2H), 3.50 (m, 2H), 3.30 (m, 2H), 3.10 (m, 2H), 2.35 (m, 2H):

MS (+ve ESI): 521 (M+H)$^+$.

EXAMPLE 34

Preparation of Compound No. 34 in Table 3

An analogous reaction to that described in example 17, but starting with 1-(4aminophenyl)phenylacetonitrile (41 mg, 0.20 mmol) and 4-chloro-6-methoxy-7-(3-morpholinopropoxy)quinazoline (67.5 mg, 0.20 mmol), yielded the title compound (96 mg, 80% yield) as a white solid:

$^1$H-NMR (DMSO d$_6$): 11.27 (s, 1H), 8.75 (s, 1H), 8.31 (s, 1H), 7.74 (d, 2H), 7.49 (d, 2H), 7.29–7.46 (m, 6H), 5.87 (s, 1H), 4.30 (t, 2H), 4.01 (s, 3H), 3.71–4.01 (m, 4H), 3.00–3.57 (m, 6H), 2.23–2.39 (m, 2H):

MS (+ve ESI): 510 (M+H)$^+$.

EXAMPLE 35

Preparation of Compound No. 35 in Table 3

An analogous reaction to that described in example 30, but starting with 4-hexylaniline (89 mg, 0.50 mmol), yielded the title compound (173 mg, 67% yield) as a white solid:

$^1$H-NMR (DMSO d$_6$): 11.43 (s, 1H), 11.18 (s, 1H), 8.78 (s, 1H), 8.38 (s, 1H), 7.60 (d, 2H), 7.43 (s, 1H), 7.30 (d, 2H), 4.32 (t, 2H), 4.03 (s, 3H), 3.75–4.03 (m, 4H), 3.00–3.60 (m, 6H), 2.62 (t, 2H), 2.28–2.42 (m, 2H), 1.53–1.68 (m, 2H), 1.21–1.40 (m, 6H), 0.88 (t, 3H):

MS (+ve ESI): 479 (M+H)$^+$.

EXAMPLE 36

Preparation of Compound No. 36 in Table 3

An analogous reaction to that described in example 30, but starting with 4-n-butylaniline (75 mg, 0.50 mmol) yielded the title compound (168 mg, 69% yield) as a white solid:

$^1$H-NMR (DMSO d$_6$): 11.40 (s, 1H), 11.15 (s, 1H), 8.80 (s, 1H), 8.40 (s, 1H), 7.60 (d, 2H), 7.42 (s, 1H), 7.3 (d, 2H), 4.32 (t, 2H), 4.04 (s, 3H), 3.95 (m, 2H), 3.85 (m, 2H), 3.50 (m, 2H), 3.35 (m, 2H), 3.10 (m, 2H), 2.65 (m, 2H), 2.35 (m, 2H), 1.60 (m, 2H), 1.35 (m, 2H), 0.91 (t, 3H):

MS (+ve ESI): 451 (M+H)$^+$.

EXAMPLE 37

Preparation of Compound No. 37 in Table 3

An analogous reaction to that described in example 30, but starting with 4-aminodiphenylmethane (92 mg, 0.50 mmol) yielded the title compound (235 mg, 90% yield) as a white solid:

$^1$H-NMR (DMSO d$_6$): 11.35 (s, 1H), 11.10 (s, 1H), 8.75 (s, 1H), 8.35 (s, 1H), 7.60 (d, 2H), 7.35 (s, 1H), 7.30 (m, 6H), 7.20 (t, 1H), 4.30 (t, 2H), 4.00 (s, 3H), 3.97 (s, 2H), 3.95 (m, 2H), 3.84 (m, 2H), 3.50 (m, 2H), 3.30 (m, 2H), 3.10 (m, 2H), 2.35 (m, 2H):

MS (+ve ESI): 485 (M+H)$^+$.

EXAMPLE 38

Preparation of Compound No. 38 in Table 3

Trifluoroacetic acid (1.00 ml, 13.1 mmol) was added to a suspension of 4-(4-(N-Boc-amino)anilino)-6-methoxy-7-(3-morpholinopropoxy)quinazoline dihydrochloride (100 mg, 0.172 mmol) in dichloromethane (2.0 ml) and the reaction stirred for 1 hour at ambient temperature. The solvents were removed in vacuo, the residue was suspended in water (2.0 ml) and saturated aqueous sodium bicarbonate solution (4.0 ml) was added. The aqueous phase was extracted with dichloromethane (3×10 ml) and the combined organic layers were washed with brine (25 ml) and evaporated in vacuo. Drying of the solid in vacuo the title compound (53 mg, 75% yield) as a white solid:

$^1$H-NMR (DMSO d$_6$): 9.19 (s, 1H), 8.30 (s, 1H), 7.79 (s, 1H), 7.25 (d, 2H), 7.10 (s, 1H), 6.60 (d, 2H), 5.00 (s, 2H), 4.15 (t, 2H), 3.90 (s, 3H), 3.60 (m, 4H), 2.45 (t, 211), 2.40 (m, 4H), 1.95 (m, 2H):

MS (–ve ESI): 408 (M–H)$^-$,

MS (+ve ESI): 410 (M+H)$^+$.

4-(4-(N-Boc-amino)anilino)-6-methoxy-7-(3-morpholinopropoxy)quinazoline dihydrochloride, used as the starting material, was obtained as follows:

A solution of N-(t-butoxycarbonyl) 4-aminoaniline (5.73 g, 27.5 mmol), and 4-chloro-6-methoxy-7-(3-morpholinopropoxy)quinazoline (8.44 g, 25.0 mmol), in isopropanol (100 ml) was heated at reflux for 3.5 hours before the reaction was allowed to cool to ambient temperature. The solid which had precipitated was collected by suction filtration and washed with diethyl ether (2×100 ml). Drying of this material yielded 4-(4-(N-Boc-amino)anilino)-6-methoxy-7-(3-morpholinopropoxy)quinazoline dihydrochloride (13.79 g, 95% yield) as a white solid:

$^1$H-NMR (DMSO d$_6$): 11.30 (s, 1H), 9.45 (s, 1H), 8.75 (s, 1H), 8.30 (s, 1H), 7.55 (s, 4H), 7.40 (s, 1H), 4.30 (t, 2H), 4.00 (s, 3H), 3.95 (m, 2H), 3.85 (m, 2H), 3.50 (m, 2H), 3.30 (m, 2H), 3.10 (m, 2H), 2.30 (m, 2H), 1.50 (s, 9H):

MS (−ve ESI): 508 (M−H)$^−$,
MS (+ve ESI): 510 (M+H)$^+$.

EXAMPLE 39

Preparation of Compound No. 39 in Table 3

An analogous reaction to that described in example 17, but starting with 4-(1-morpholino)aniline (45 mg, 0.25 mmol) yielded the title compound (120 mg, 99% yield) as a white solid:

$^1$H-NMR (DMSO d$_6$): 11.33(s, 1H), 8.75 (s, 1H), 8.30 (s, 1H), 7.53 (d, 2H), 7.37 (s, 1H), 7.05 (d, 2H), 4.30 (t, 2H), 4.00 (s, 3H), 3.99 (m, 2H), 3.82 (m, 2H), 3.75 (m, 4H), 3.50 (m, 2H), 3.25 (m, 2H), 3.15 (m, 4H), 3.10 (m, 2H), 2.35 (m, 2H):

MS (+ve ESI): 480 (M+H)$^+$.

EXAMPLE 40

Preparation of Compound No. 40 in Table 3

An analogous reaction to that described in example 17, but starting with 1-(4-aminophenyl)piperidine (44 mg, 0.25 mmol) yielded the title compound (88 mg, 72% yield) as a white solid:

$^1$H-NMR (DMSO d$_6$): 8.70 (s, 1H), 8.23 (s, 1H), 7.47–7.60 (m, 2H), 7.33 (s, 1H), 7.00–7.18 (m, 2H), 4.28 (t, 2H), 4.00 (s, 3H), 3.70–4.00 (m, 4H), 2.98–3.58 (m, 8H), 2.21–2.37 (m, 2H), 1.48–1.73 (m, 6H):

MS (+ve ESI): 478 (M+H)$^+$.

EXAMPLE 41

Preparation of Compound No. 41 in Table 4

2-Picolyl chloride hydrochloride (260 mg, 1.59 mmol) was added to a suspension of potassium carbonate (796 mg, 5.77 mmol), potassium iodide (358 mg, 2.16 mmol) and 4-(4-hydroxy-3-methylanilino)-6,7-dimethoxyquinazoline (500 mg, 1.92 mmol) in acetone (25 ml) and the reaction heated at reflux for 18 hours. The reaction was cooled, filtered and the filtrate evaporated in vacuo. Purification by flash chromatography on silica gel, eluting with 0–4% methanol in dichloromethane, yielded the title compound (436 mg, 68% yield) as a white solid:

$^1$H-NMR (DMSO d$_6$): 11.36 (s, 1H), 8.69 (d, 1H, J=6 Hz), 8.30 (s, 1H), 8.09 (dt, 1H, J=2,7 Hz), 7.74 (d, 2H, J=8 Hz), 7.57 (m, 1H), 7.41–7.45 (m, 2H), 7.34 (s, 1H), 7.09 (d, 1H, J=8 Hz), 5.34 (s, 2H), 3.99 (s, 3H), 3.97 (s, 3H), 2.28 (s, 3H):

MS (−ve ESI): 401 (M−H)$^−$,
MS (+ve ESI): 403 (M+H)$^+$.

4-(4-hydroxy-3-methylanilino)-6,7-dimethoxyquinazoline, used as starting material, was obtained as follows:—

An analogous reaction to that described in example 17, but starting with 4-amino-2-methylphenol (6.98 g, 56.7 mmol) and 4-chloro-6,7-dimethoxyquinazoline hydrochloride (14.79 g, 56.7 mmol), yielded 4-(4-hydroxy-3-methylanilino)-6,7-dimethoxyquinazoline (17.72 g, 90% yield) as a white solid:

MS (+ve CI): 312 (M+H)$^+$.

EXAMPLE 42

Preparation of Compound No. 42 in Table 4

An analogous reaction to that described in example 17, but starting with 3-methyl-4-((4-methyl-2-pyridyl)methoxy) aniline (400 mg, 1.5 mmol) yielded the title compound (294 mg, 47% yield) as an off-white solid:

$^1$H-NMR (DMSO d$_6$): 11.36 (s, 1H), 8.76 (s, 1H), 8.62 (d, 1H, J=7 Hz), 8.30 (s, 1H), 7.71 (s, 1H), 7.54 (d, 1H, J=8 Hz), 7.44 (m, 2H), 7.34 (s, 1H), 7.10 (d, 1H, J=8 Hz), 5.36 (s, 2H), 3.99 (s, 3H), 3.97 (s, 3H), 2.44 (s, 3H), 2.28 (s, 3H):

MS (+ve ESI): 417 (M+H)$^+$.

3-Methyl-4-((4-methyl-2-pyridyl)methoxy)aniline, used as starting material, was obtained as follows:— a) n-Butyllithium (24 ml of a 1.6 N solution in hexanes, 38.4 mmol) was added to a stirred solution of 2,4-lutidine (4.28 g, 40 mmol) in tetrahydrofuran (70 ml) at −70° C. under an inert atmosphere. After 1 hour, air was bubbled through (for 1 hour), methanol (50 ml) was added and the reaction allowed to warm to ambient temperature. The reaction mixture was filtered and then evaporated in vacuo. Purification of the crude product by flash chromatography on silica gel, eluting with ethyl acetate, yielded 2-(hydroxymethyl)-4-picoline (700 mg, 14% yield) as a white solid.

b) Sodium hydride (150 mg of an 80% dispersion in mineral oil, 5.00 mmol) was added to a stirred solution of 2-(hydroxymethyl)-4-picoline (590 mg, 5.00 mmol) in N-methylpyrrolidine (20 ml) at ambient temperature. 2-Fluoro-5-nitrotoluene (775 mg, 5.00 mmol) was added, the reaction was stirred for 18 hours at ambient temperature and the reaction was poured into water (60 ml). Collection of the yellow solid which precipitated, followed by drying in vacuo, yielded 2-((4-methyl-2-pyridyl)methoxy)-5-nitrotoluene (900 mg, 70% yield) as a yellow solid.

c) 5% Platinum on carbon (50 mg) was added to a solution of 2-((4-methyl-2-pyridyl)methoxy)-5-nitrotoluene (750 mg, 2.91 mmol) in ethanol (150 ml) and the solution was stirred for 2 hours at ambient temperature under an atmosphere of hydrogen. Filtration of the reaction mixture, followed by solvent evaporation in vacuo, yielded 3-methyl-4-((4-methyl-2-pyridyl)methoxy)aniline (420 mg, 63% yield) as a yellow gum.

EXAMPLE 43

Preparation of Compound No. 43 in Table 4

An analogous reaction to that described in example 17, but starting with 3-methyl-4-((4-methoxy-2-pyridyl)methoxy)aniline (670 mg, 2.75 mmol) yielded the title compound (290 mg, 24% yield) as a brown solid:

$^1$H-NMR (DMSO d$_6$): 9.60 (s, 1H), 8.43 (s, 1H), 8.39 (d, 1H, J=7 Hz), 7.85 (s, 1H), 7.48 (m, 2H), 7.15 (s, 1H), 7.02 (d, 1H, J=2 Hz), 6.97 (d, 1H, J=8 Hz), 6.92 (dd, 1H, J=2,8 Hz), 5.14 (s, 2H), 3.93 (s, 3H), 3.91 (s, 3H), 3.83 (s, 3H), 2.27 (s, 3H):

MS (−ve ESI): 431 (M−H)$^−$,
MS (+ve ESI): 433 (M+H)$^+$.

3-Methyl-4-((4-methoxy-2-pyridyl)methoxy)aniline, used as starting material, was obtained as follows a) A solution of 2-picolinic acid (10.7 g, 87 mmol) in thionyl chloride (50 ml) was heated at reflux for 18 hours before being cooled and evaporated in vacuo. The residue was treated with methanol (25 ml) and then added to a solution of sodium methoxide prepared from sodium (1.0 g, 43 mmol) and methanol (100 ml). The reaction was heated at reflux for 3 hours, cooled and evaporated in vacuo. The residue was partitioned between water and ethyl acetate and the organic phase was separated. Evaporation of the organic phase yielded methyl 4-methoxypicoline-2-carboxylate (6.00 g, 41% yield) as a white solid.

b) Lithium aluminum hydride (16 ml of a 1.0 N solution in diethyl ether, 16 mmol) was added to a solution of methyl 4-methoxypicoline-2-carboxylate (2.70 g, 16 mmol) in diethyl ether (50 ml) at ambient temperature. The reaction was stirred for 1 hour, poured into an aqueous solution of Rochelle's salt (250 ml) and the reaction mixture extracted with ethyl acetate (3×50 ml). Purification of the crude product by flash chromatography on silica gel, eluting with dichloromethane-ethyl acetate, yielded 2-(hydroxymethyl)-4-methoxypyridine (800 mg, 36% yield) as a white solid.

c) An analogous reaction to that described in example 42b, but starting with 2-(hydroxymethyl)-4-methoxypyridine (600 mg, 4.30 mmol), yielded 2-((4-methoxy-2-pyridyl)methoxy)-5-nitrotoluene (780 mg, 70% yield) as a yellow solid.

d) An analogous reaction to that described in example 42c, but starting with 2-((4-methoxy-2-pyridyl)methoxy)-5-nitrotoluene (770 mg, 2.96 mmol) yielded 3-methyl-4-((4-methoxy-2-pyridyl)methoxy)aniline (680 mg, 99% yield) as a yellow solid.

EXAMPLE 44

Preparation of Compound No. 44 in Table 4

An analogous reaction to that described in example 17, but starting with 3-methyl-4-((6-methyl-2-pyridyl)methoxy)aniline (1.50 g, 6.14 mmol) yielded the title compound (748 mg, 29% yield) as a white solid:

$^1$H-NMR (DMSO $d_6$): 11.40 (s, 1H), 8.76 (s, 1H), 8.32 (s, 1H), 8.13 (t, 1H, J=7 Hz), 7.67 (d, 1H, J=8 Hz), 7.56 (d, 1H, J=8 Hz), 7.45 (m, 2H), 7.35 (s, 1H), 7.09 (d, 1H, J=8 Hz), 5.38 (s, 2H), 4.00 (s, 3H), 3.97 (s, 3H), 2.65 (s, 3H), 2.28 (s, 3H):

MS (−ve ESI): 415 (M−H)$^-$,

MS (+ve ESI): 417 (M+H)$^+$.

3-Methyl-4-((6-methyl-2-pyridyl)methoxy)aniline, used as starting material, was obtained as follows:— a) An analogous reaction to that described in example 42b, but starting with 2-(hydroxymethyl)-6-methylpyridine (2.43 g, 20 mmol), yielded 2-((6-methyl-2-pyridyl)methoxy)-5-nitrotoluene (2.70 g, 52% yield) as a yellow solid.

b) An analogous reaction to that described in example 42c, but starting with 2-((6-methyl-2-pyridyl)methoxy)-5-nitrotoluene (400 mg, 1.55 mmol) yielded 3-methyl-4-((6-methyl-2-pyridyl)methoxy)aniline (300 mg, 85% yield) as a yellow gum.

EXAMPLE 45

Preparation of Compound No. 45 in Table 4

An analogous reaction to that described in example 17, but starting with 4-chloro-6-methoxy-7-(2,2,2-trifluoroethoxy)quinazoline (572 mg, 1.96 mmol) and 3-fluoro-4-(2-pyridylmethoxy)-aniline (469 mg, 2.15 mmol) yielded the title compound (315 mg, 34% yield) as a white solid:

$^1$H-NMR (DMSO $d_6$): 11.59 (s, 1H), 8.83 (s, 1H), 8.65 (d, 2H, J=5 Hz), 7.88 (dt, 1H, J=1,7 Hz), 7.72 (dd, 1H, J=2,8 Hz), 7.56 (d, 1H, J=8 Hz), 7.29–7.46 (m, 4H), 5.30 (s, 2H), 5.05 (q, 2H, J=8 Hz), 4.04 (s, 3H):

MS (−ve ESI): 473 (M−H)$^-$,

MS (+ve ESI): 475 (M+H)$^+$.

4-Chloro-6-methoxy-7-(2,2,2-trifluoroethoxy)quinazoline, used as starting material was obtained as follows:

a) Potassium carbonate (62.2 g, 450 mmol) was added to a solution of ethyl vanillate (58.9 g, 300 mmol) in dimethylformamide (400 ml) and the reaction heated to 120° C. 2,2,2-Trifluoroethyl methanesulphonate (63.4 g, 360 mmol) was added over 15 minutes and the reaction heated at 120° C. for 15 hours. The reaction was cooled to ambient temperature, diethyl ether (400 ml) was added and the reaction was filtered. The filtrate was evaporated in vacuo and the residue was taken up in a mixture of diethyl ether (375 ml) and isohexane (375 ml). The organic layer was concentrated in vacuo to a total volume of 250 ml and the solid which crystallised out was collected by suction filtration. Drying of the solid in vacuo yielded ethyl 4-(2,2,2-trifluoroethoxy)-3-methoxybenzoate (43.0 g, 52% yield) as a white crystalline solid:

$^1$H-NMR (DMSO $d_6$): 7.57 (dd, 1H, J=2, 8 Hz), 7.49 (d, 1H, J=2 Hz), 7.18 (d, 1H, J=8 Hz), 5.81 (q, 2H, J=7 Hz), 5.29 (q, 2H, J=7 Hz), 3.82 (s, 3H), 1.30 (t, 3H, J=7 Hz):

MS (+ve ESI): 279 (M+H)$^+$.

b) Concentrated sulphuric acid (64 ml) and concentrated nitric acid (10.0 ml, 0.152 mol) were added cautiously, over 1 hour, to a two-phase system containing a stirred solution yielded ethyl 4-(2,2,2-trifluoroethoxy)-3-methoxybenzoate (35.3 g, 0.127 mmol) in dichloromethane (340 ml), acetic acid (173 ml) and water (40 ml) at 5° C. The reaction was allowed to warm to ambient temperature over 60 hours (with vigorous mechanical stirring), the aqueous phase was separated, and the organic phase washed with water (6×250 ml). The organic phase was concentrated to a total volume of ~200 ml, isohexane (150 ml) was added and the solid which precipitated out was collected by suction filtration. Drying of the solid in vacuo_yielded ethyl 3-methoxy-4-(2,2,2-trifluoroethoxy)-6-nitrobenzoate (21.7 g, 52% yield) as a yellow solid. The mother liquors contained a mixture of product (28%) and starting material (72%) which was recycled in a latter reaction:

$^1$H-NMR (DMSO $d_6$): 7.80 (s, 1H), 7.42 (s, 1H), 4.90 (q, 2H, J=7 Hz), 4.20–4.35 (m, 2H), 4.00 (s, 3H), 1.32 (t, 3H, J=7 Hz):

MS (+ve ESI): 324 (M+H)$^+$.

c) A suspension of ethyl 3-methoxy-4-(2,2,2-trifluoroethoxy)-6-nitrobenzoate (24.0 g, 74.3 mmol) and 10% palladium on carbon (3.0 g) in a mixture of ethanol (100 ml) and ethyl acetate (750 ml) was stirred under an atmosphere of hydrogen for 18 hours. Removal of the catalyst by filtration, followed by solvent evaporation in vacuo yielded ethyl 3-methoxy-4-(2,2,2-trifluoroethoxy)-6-aminobenzoate (20.2 g, 93% yield) as a pale brown solid:

¹H-NMR (DMSO d₆): 7.20 (s, 1H), 6.45 (s, 1H), 6.40 (s, 2H), 5.70 (q, 2H, J=7 Hz), 4.20 (q, 2H, J=7 Hz), 3.65 (s, 3H), 1.32 (t, 3H, J=7 Hz):
MS (−ve ESI): 292 (M−H)⁻,
MS (+ve ESI): 294 (M+H)⁺.

d) A mixture of ethyl 2-amino-4-(2,2,2-trifluoroethoxy)-5-methoxybenzoate (20.2 g, 69.1 mmol) and formamide (50 ml) was heated at 175° C. for 6 hours. The mixture was allowed to cool to ambient temperature, ethanol (150 ml) was added and the reaction allowed to stand for 18 hours. Collection of the solid which had precipitated by suction filtration, followed by washing with ethanol (2×50 ml) and drying in vacuo, yielded 6-methoxy-7-(2,2,2-trifluoroethoxy)-3,4-dihydroquinazolin-4-one (15.8 g, 84% yield) as a pale brown crystalline solid:
¹H-NMR (DMSO d₆): 12.10 (s, 1H), 8.00 (s, 1H), 7.51 (s, 1H), 7.30 (s, 1H), 4.90 (q, 2H, J=7 Hz), 3.90 (s, 3H):
MS (−ve ESI): 273 (M−H)⁻,
MS (+ve ESI): 275 (M+H)⁺.

e) Dimethylformamide (0.1 ml) was added dropwise to a solution of 6-methoxy-7-(2,2,2-trifluoroethoxy)-3,4-dihydroquinazolin-4-one (15.8 g, 57.7 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6-methoxy-7-(2,2,2-trifluoroethoxy)quinazoline (16.3 g, 97% yield) as a cream solid:
¹H-NMR (DMSO d₆): 8.95 (s, 1H), 7.65 (s, 1H), 7.25 (s, 1H), 5.05 (q, 2H, J=7 Hz), 4.00 (s, 3H):
MS (+ve-ESI): 293, 295 (M+H)⁺.

EXAMPLE 46

Preparation of Compound No. 46 in Table 4

An analogous reaction to that described in example 17, but starting with 4-chloro-6-methoxy-7-(3-morpholinopropoxy)quinazoline (74 mg, 0.22 mmol) and (4-amino-2-chlorophenyl)-4-chlorophenylether (70 mg, 0.24 mmol) yielded the title compound (115 mg, 86% yield) as a white solid:
¹H-NMR (DMSO d₆): 8.82 (s, 1H), 8.35 (s, 1H), 8.11 (d, 1H), 7.79 (dd, 1H), 7.43 (d, 2H), 7.38 (s, 1H), 7.28 (d, 1H), 7.00 (d, 2H), 4.32 (t, 2H), 4.02 (s, 3H), 3.99 (m, 2H), 3.80 (m, 2H), 3.48 (m, 2H), 3.30 (m, 2H), 3.11 (m, 2H), 2.30 (m, 2H):
MS (+ve ESI): 555 (M+H)⁺.

4-Chloro-6-methoxy-7-(3-morpholinopropoxy)quinazoline, used as the starting material, was obtained as follows:

a) A mixture of morpholine (261 ml, 3.00 mol) and 1-bromo-3-chloropropane (148 ml, 1.50 mol) in toluene (900 ml) was stirred for 18 hours at ambient temperature. Additional 1-bromo-3-chloropropane (25 ml, 0.25 mol) was added, the reaction was stirred for a further 1 hour and then filtered to remove the precipitated solid before the filtrate was concentrated in vacuo. Distillation of the crude oil yielded N-(3-chloropropyl)-morpholine (119.3 g, 49% yield) as the fraction boiling at 70–80° C./2.6 mmHg:
¹H-NMR (DMSO d₆): 3.65 (t, 2H), 3.55 (m, 4H), 2.40 (t, 2H), 2.39 (m, 4H), 1.85 (m, 2H):
MS (+ve ESI): 164 (M+H)⁺.

b) N-(3-Chloropropyl)morpholine (90 g, 0.55 mol) was added dropwise, over 30 minutes, to a solution of ethyl vanillate (98 g, 0.50 mol) and powdered potassium carbonate (104 g, 0.75 mol) in dimethylformamide (300 ml) at 80° C. The reaction was heated at 80° C. for 90 minutes, cooled to ambient temperature, filtered and the filtrate concentrated in vacuo. The crude product was taken up in diethyl ether (1000 ml), filtered and washed with water (2×200 ml) and brine (200 ml). Solvent evaporation in vacuo yielded ethyl 3-methoxy-4-(3-morpholinopropoxy)benzoate (161.5 g, 100% yield) as a pale yellow oil which crystallised on standing to afford a pale yellow solid:
¹H-NMR (DMSO d₆): 7.55 (dd, 1H), 7.40 (d, 1H), 7.05 (d, 1H), 4.30 (q, 2H), 4.05 (t, 2H), 3.80 (s, 3H), 3.55 (m, 4H), 2.40 (t, 2H), 2.35 (m, 4H), 1.90 (m, 2H), 1.30 (t, 3H):
MS (−ve ESI): 324 (M−H)⁻, c) Concentrated sulphuric acid (110 ml) and concentrated nitric acid (19.0 ml, 0.289 mol) were added cautiously, over a 50 minute period, to a two-phase system containing a stirred solution of ethyl 3-methoxy-4-(3-morpholinopropoxy)benzoate (76.5 g, 0.237 mol) in dichloromethane (600 ml), acetic acid (300 ml) and water (70 ml) at 5° C. The reaction was allowed to warm to ambient temperature over 18 hours, the aqueous phase was separated, and the aqueous phase was taken to pH 9 by addition of 40% aqueous sodium hydroxide solution (775 ml). Extraction of the aqueous phase with dichloromethane (3×600 ml) and subsequent solvent evaporation in vacuo_yielded ethyl 3-methoxy-4-(3-morpholinopropoxy)-6-nitrobenzoate (141.3 g, 86% yield) as a yellow gum:
¹H-NMR (CDCl₃): 7.50 (s, 1H), 7.10 (s, 1H), 4.40 (q, 2H), 4.20 (t, 2H), 4.00 (s, 3H), 3.70 (m, 4H), 2.50 (t, 2H13, 2.45 (m, 4H), 2.05 (m, 2H), 1.40 (t, 3H):
MS (+ve ESI): 369 (M+H)⁺.

d) A suspension of ethyl 3-methoxy-4-(3-morpholinopropoxy)-6-nitrobenzoate (132.2 g, 359 mmol) and 10% palladium on carbon (3.0 g) in a mixture of ethanol (200 ml) and ethyl acetate (2000 ml) was stirred under an atmosphere of hydrogen for 18 hours. Removal of the catalyst by filtration, followed by solvent evaporation in vacuo yielded ethyl 3-methoxy-4-(3-morpholinopropoxy)-6-aminobenzoate (122 g, 100% yield) as a brown oil:
¹H-NMR (DMSO d₆): 7.15 (s, 1H), 6.40 (s, 2H), 6.35 (s, 1H), 4.20 (q, 2H), 3.95 (t, 2H), 3.65 (s, 3H), 3.55 (m, 4H), 2.40 (t, 2H), 2.35 (m, 4H), 1.85 (m, 2H), 1.25 (t, 3H):
MS (−ve ESI): 337 (M−H)⁻;
MS (+ve ESI): 339 (M+H)⁺.

e) A solution of ethyl 3-methoxy-4-(3-morpholinopropoxy)-6-aminobenzoate (130 g, 384 mmol) in formamide (280 ml) was heated at 180° C. for 3 hours, during which time a small amount (25 ml) of liquid distilled out of the reaction. The reaction was cooled to 125° C. and the excess formamide was evaporated in vacuo. Trituration of the solid residue with isopropanol (100 ml), followed by drying in vacuo, yielded 6-methoxy-7-(3-morpholinopropoxy)-3,4-dihydroquinazolin-4-one (83.0 g, 68% yield) as a pale brown solid:
¹H-NMR (DMSO d₆): 12.00 (s, 1H), 7.95 (s, 1H), 7.45 (s, 1H), 7.10 (s, 1H), 4.15 (t, 2H), 3.85 (s, 3H), 3.60 (m, 4H), 2.45 (t, 2H), 2.35 (m, 4H), 1.90 (m, 2H):
MS (−ve ESI): 318 (M−H)⁻,
MS (+ve ESI): 320 (M+H)⁺.

f) Dimethylformamide (2.0 ml) was added dropwise to a solution of 6-methoxy-7-(3-morpholinopropoxy)-3,4-dihydro-quinazolin-4-one (83.0 g, 261 mmol) in thionyl chloride (700 ml) and the reaction was heated at reflux for 3.5 hours. The reaction was cooled, excess thionyl chloride was removed in vacuo, the residue was taken up in water (500 ml) and this aqueous solution was taken to pH 9 by addition of saturated aqueous sodium bicarbonate solution (300 ml). The aqueous phase was extracted with dichloromethane (2×400 ml), the organic solution was washed with brine (400 ml) and the solvents were removed in vacuo. Trituration of the solid residue with ethyl acetate (150 ml), followed by drying in vacuo, yielded 4-chloro-6-methoxy-7-(3-morpholinopropoxy)quinazoline (53 g, 60% yield) as a pale brown solid:

$^1$H-NMR (CDCl$_3$): 8.85 (s, 1H), 7.39 (s, 1H), 7.38 (s, 1H), 4.30 (t, 2H), 4.05 (s, 3H), 3.70 (m, 4H), 2.60 (t, 2H), 2.50 (m, 4H), 2.10 (m, 2H):

MS (+ve ESI): 338 (M+H)$^+$.

EXAMPLE 47

Preparation of Compound No. 47 in Table 4

An analogous reaction to that described in example 17, but starting with (4-amino-2,6-dichlorophenyl)-4-chlorophenylsulphide (73 mg, 0.24 mmol) yielded the title compound (118 mg, 86% yield) as a white solid:

$^1$H-NMR (DMSO d$_6$):8.92 (s, 1H), 8.41 (s, 1H), 8.38 (s, 2H), 7.40 (s, 1H), 7.39 (d, 2H), 7.10 (d, 2H), 4.30 (t, 2H), 4.03 (s, 3H), 4.00 (m, 2H), 3.80 (m, 2H), 3.50 (m, 2H), 3.28 (m, 2H), 3.10 (m, 2H), 2.30 (m, 2H):

MS (−ve ESI): 603 (M−H)$^−$.

EXAMPLE 48

Preparation of Compound No. 48 in Table 4

An analogous reaction to that described in example 17, but starting with 4-chloro-6-acetoxy-7-methoxyquinazoline (150 mg, 0.60 mmol) and 3-fluoro-4-(2-pyridylmethoxy)-aniline (142 mg, 0.65 mmol) yielded the title compound (200 mg, 77% yield) as a white solid:

$^1$H-NMR (DMSO d$_6$): 11.06 (s, 1H), 8.85 (s, 1H), 8.59 (m, 2H), 7.88 (dt, 1H, J=1,7 Hz), 7.72 (dd, 1H, J=2,8 Hz), 7.56 (d, 1H, J=8 Hz), 7.29–7.46 (m, 4H), 5.30 (s, 2H), 3.99 (s, 3H), 2.37 (s, 3H):

MS (−ve ESI): 433 (M−H)$^−$,
MS (+ve ESI): 435 (M+H)$^+$.

4-chloro-6-acetoxy-7-methoxyquinazoline and 3-fluoro-4-((2-pyridyl)methoxy)aniline, used as the starting materials, were obtained as follows:

a) A mixture of 6,7-dimethoxy-3,4-dihydroquinazolin-4-one (20.0 g, 97 mmol) and racemic methionine (21.7 g, 146 mmol) in methanesulphonic acid (150 ml) were heated at 100° C. for 5.5 hours and then allowed to cool to ambient temperature over 18 hours. The reaction was poured into cold water (750 ml), the pH of the aqueous solution was adjusted to pH 6 (by addition of 2.0N aqueous sodium hydroxide solution) and the solid which formed was collected by suction filtration. The solid was dried in vacuo and then dissolved in a mixture of pyridine (20 ml) and acetic anhydride (150 ml). The solution was heated at 100° C. for 1 hour, cooled and poured into cold water (1050 ml). Collection of the resultant solid by suction filtration, followed by drying in vacuo, yielded 6-acetoxy-7-methoxy-3,4-dihydro-quinazolin-4-one (13.9 g, 57% yield) as a pale-brown solid:

$^1$H-NMR (DMSO d$_6$): 12.16 (s, 1H), 8.05 (s, 1H), 7.75 (s, 1H), 3.90 (s, 3H), 2.25 (s, 3H):

MS (−ve ESI): 233 (M−H)$^−$, b) Dimethylformamide (0.25 ml) was added dropwise to a solution of 6-acetoxy-7-methoxy-3,4-dihydro-quinazolin-4-one (13.8 g, 59.0 mmol) in thionyl chloride (150 ml) and the reaction was heated at reflux for 1.5 hours. The reaction was cooled, excess thionyl chloride was removed in vacuo and the residue was azeotroped with toluene (2×50 ml) to remove the last of the thionyl chloride. Drying in vacuo yielded 4-chloro-6-acetoxy-7-methoxyquinazoline hydrochloride (14.7 g, 87% yield) as a beige solid, which was used without further purification:

$^1$H-NMR (DMSO d$_6$): 9.00 (s, 1H), 8.00 (s, 1H), 7.60 (s, 1H), 4.00 (s, 3H), 2.35 (s, 3H):

MS (+ve ESI): 253 (M+H)$^+$.

c) An analogous reaction to that described in example 42b, but starting with 2-(hydroxymethyl)pyridine (3.50 g, 36 mmol) and 3,4-difluoronitrobenzene (5.00 g, 31.4 mmol), yielded 2-((2-pyridyl)methoxy)-5-nitrofluorobenzene (4.50 g, 58% yield) as a yellow solid.

d) An analogous reaction to that described in example 42c, but starting with 2-((2-pyridyl)methoxy)-5-nitrofluorobenzene (4.5 g, 18.1 mmol), yielded 3-fluoro-4-((2-pyridyl)methoxy)aniline (1.86 g, 47% yield) as a yellow solid.

EXAMPLE 49

Preparation of Compound No. 49 in Table 5

An analogous reaction to that described in example 30 but starting 3-aminoquinoline (72 mg, 0.50 mmol) and 4-chloro-6-methoxy-7-(3-morpholinopropoxy)quinazoline (168 mg, 0.50 mmol) yielded the title compound (232 mg, 97% yield) as a white solid:

$^1$H-NMR (DMSO d$_6$): 11.97 (s, 1H), 11.11 (s, 1H), 9.33 (s, 1H), 8.89 (s, 1H), 8.74 (s, 1H), 8.57 (s, 1H), 8.10 (d, 1H), 8.05 (d, 1H), 7.81 (t, 1H), 7.69 (t, 1H), 7.46 (s, 1H), 4.34 (t, 2H), 4.09 (s, 3H), 3.77–4.09 (m, 4H), 2.82–3.17 (m, 6H), 2.26–2.43 (m, 2H):

MS (+ve ESI): 446 (M+H)$^+$.

Biological Data

The compounds of the invention inhibit the serine/threonine kinase activity of the aurora2 kinase and thus inhibit the cell cycle and cell proliferation. These properties may be assessed, for example, using one or more of the procedures set out below:

(a) In Vitro Aurora2 Kinase Inhibition Test

This assay determines the ability of a test compound to inhibit serine/threonine kinase activity. DNA encoding aurora2 may be obtained by total gene synthesis or by cloning. This DNA may then be expressed in a suitable expression system to obtain polypeptide with serine/threonine kinase activity. In the case of aurora2, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the aurora2 coding sequence. This allowed the insertion of the aurora2 gene in frame with the 6 histidine residues, spacer region and rTEV protease cleavage site encoded by the pFastBac HTc vector. The 3' PCR primer replaced the aurora2 stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemaglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged aurora2 protein. Details of the methods for the assembly of recombinant DNA molecules can be found in standard texts, for example Sambrook et al. 1989, Molecular Cloning—A Laboratory Manual, $2^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora2 gene was transformed into *E. coli* DH10Bac cells containing the baculovirus genome (bacmid DNA) and via a transposition event in the cells, a region of the pFastBac vector containing gentamycin resistance gene and the aurora2 gene including the baculovirus polyhedrin promoter was transposed directly into the bacmid DNA. By selection on gentamycin, kanamycin, tetracycline and X-gal, resultant white colonies should contain recombinant bacmid DNA encoding aurora2. Bacmid DNA was extracted from a small scale culture of several BH10Bac white colonies and transfected into *Spodoptera frugiperda* Sf21 cells grown in TC 100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1 \times 10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant aurora2 protein.

For the large scale expression of aurora2 kinase activity, Sf21 insect cells were grown at 28° C. in TC 100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure aurora2 recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per 3×1 cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora2 protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora2 kinase, was dialysed exhaustively against dialysis-buffer (25 mM HEPES pH7.4 at 4° C., 45% glycerol (v/v), 100 mM KCl, 0.25% Nonidet P40 (v/v), 1 mM dithiothreitol).

Each new batch of aurora2 enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent & 20 µl of dilute enzyme is used for each assay well. Test compounds (at 10 mM in dimethylsulphoxide (DMSO)) were diluted with water & 10 µl of diluted compound was transferred to wells in the assay plates. "Total" & "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM MnCl$_2$, 6.25 mM ATP, 7.5 µM peptide substrate [biotin-LRRWSLGLRRWS-LGLRRWSLGLRRWSLG]) containing 0.2 µCi [γ$^{33}$P]ATP (Amersham Pharmacia, specific activity ≧2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity.

In this test, compound 43 in Table 4 gave 50% inhibition of enzyme activity at a concentration of 0.465 µM and compound 29 in Table 3 gave 50% inhibition of enzyme activity at a concentration of 0.069 µM.

(b) In Vitro Cell Proliferation Assay

These and other assays can be used to determine the ability of a test compound to inhibit the growth of adherent mammalian cell lines, for example the human tumour cell line MCF7.

Assay 1: MCF-7 (ATCC HTB-22) or other adherent cells were typically seeded at $1 \times 10^3$ cells per well (excluding the peripheral wells) in DMEM (Sigma Aldrich) without phenol red, plus 10% foetal calf serum, 1% L-glutamine and 1% penicillin/streptomycin in 96 well tissue culture treated clear plates (Costar). The following day (day 1), the media was removed from a no treatment control plate and the plate stored at −80° C. The remaining plates were dosed with compound (diluted from 10 mM stock in DMSO using DMEM (without phenol red, 10% FCS, 1% L-glutamine, 1% penicillin/streptomycin). Untreated control wells were included on each plate. After 3 days in the presence/absence of compound (day 4) the media was removed and the plates stored at −80° C. Twenty four hours later the plates were thawed at room temperature and cell density determined using the CyQUANT cell proliferation assay kit (c-7026/c-7027 Molecular Probes Inc.) according to manufacturers directions. Briefly, 200 µl of a cell lysis/dye mixture (10 µl of 20× cell lysis buffer B, 190 µl of sterile water, 0.25 µl of CYQUANT GR dye) was added to each well and the plates incubated at room temperature for 5 minutes in the dark. The fluorescence of the wells was then measured using a fluorescence microplate reader (gain 70, 2 reads per well, 1 cycle with excitation 485 nm and emission 530 nm using a CytoFluor plate reader (PerSeptive Biosystems Inc.)). The values from day 1 and day 4 (compound treated) together with the values from the untreated cells were used to determine the dilution range of a test compound that gave 50% inhibition of cell proliferation. Compound no. 43 in Table 4 was effective in this test at 12.41M and Compound no. 29 in Table 3 was effective at 2.89 µM.

These values could also be used to calculate the dilution range of a test compound at which the cell density dropped below the day 1 control value. This indicates the cytotoxicity of the compound.

Assay 2: This assay determines the ability of at test compound to inhibit the incorporation of the thymidine analogue, 5'-bromo-2'-deoxy-uridine (BrdU) into cellular DNA. MCF-7 or other adherent cells were typically seeded at $0.8 \times 10^4$ cells per well in DMEM (Sigma Aldrich) without phenol red, plus 10% foetal calf serum, 1% L-glutamine and 1% penicillin/streptomycin (50 µl/well) in 96 well tissue culture treated 96 well plates (Costar) and allowed to adhere overnight. The following day the cells were dosed with compound (diluted from 10 mM stock in DMSO using DMEM (without phenol red, 10% FCS, 1% L-glutamine, 1% penicillin/streptomycin). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 µl of BrdU labelling reagent (diluted 1:100 in media—DMEM no phenol red, 10% FCS, 1% L-glutamine, 1% penicillin/streptomycin) was added to each well and the plate returned to a humidified (+5% $CO_2$) 37° C. incubator for 2 hours. After 2 hours the labelling reagent was removed by decanting and tapping the plate on a paper towel. FixDenat solution (50 µl per well) was added and the plates incubated at room temperature for 45 mins with shaking. The FixDenat solution was removed by decanting and tapping the inverted plate on a paper towel. The plate was then washed once with phosphate buffered saline (PBS) and 100 µl/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 5 times with PBS before being blotted dry. TMB substrate solution was added (100 µl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. Compound. no. 29 in table 3 was active at 3.68 µM in this test.

(c) In Vitro Cell Cycle Analysis Assay

This assay determines the ability of a test compound to arrest cells in specific phases of the cell cycle. Many different mammalian cell lines could be used in this assay and MCF7 cells are included here as an example. MCF-7 cells were seeded at $3 \times 10^5$ cells per T25 flask (Costar) in 5 ml DMEM (no phenol red 10% FCS, 1% L-glutamine 1% penicillin/streptomycin). Flasks were then incubated overnight in a humidified 37° C. incubator with 5% $CO_2$. The following day 1 ml of DMEM (no phenol red 10% FCS, 1% L-glutamine 1% penicillin/streptomycin) carrying the appropriate concentration of test compound solubilised in DMSO was added to the flask. A no compound control treatments was also included (0.5% DMSO). The cells were then incubated for a defined time (usually 24 hours) with compound. After this time the media was aspirated from the cells and they were washed with 5 ml of prewarmed (37° C.) sterile PBSA, then detached from the flask by brief incubation with trypsin and followed by resuspension in 10 ml of 1% Bovine Serum Albumin (BSA, Sigma-Aldrich Co.) in sterile PBSA. The samples were then centrifuged at 2200 rpm for 10 min. The supernatant was aspirated and the cell pellet was resuspended in 200%1 of 0.1% (w/v) Tris sodium citrate, 0.0564% (w/v) NaCl, 0.03% (v/v) Nonidet NP40, [pH 7.6]. Propridium Iodide (Sigma Aldrich Co.) was added to 40 µg/ml and RNAase A (Sigma Aldrich Co.) to 100 µg/ml. The cells were then incubated at 37° C. for 30 minutes. The samples were centrifuged at 2200 rpm for 10 min, the supernatant removed and the remaining pellet (nuclei) resuspended in 200%1 of sterile PBSA. Each sample was then syringed 10 times using 21 gauge needle. The samples were then transferred to LPS tubes and DNA content per cell analysed by Fluorescence activated cell sorting (FACS) using a FACScan flow cytometer (Becton Dickinson). Typically 25000 events were counted and recorded using CellQuest v1.1 software (Verity Software). Cell cycle distribution of the population was calculated using Modfit software (Verity Software) and expressed as percentage of cells in G0/G1, S and G2/M phases of the cell cycle.

Treating MCF7 cells with 24.8 µM Compound no. 43 in Table 4 for 24 hours produced the following changes in cell cycle distribution:

| Treatment | % Cells in G1 | % Cells in S | % Cells in G2/M |
|---|---|---|---|
| DMSO (control) | 60.96 | 26.99 | 12.05 |
| 24.8 µM Compound 43 | 37.29 | 33.93 | 28.78 |

Treating MCF7 cells with 5.780 µM Compound no. 29 in Table 3 for 24 hours produced the following changes in cell cycle distribution:

| Treatment | % Cells in G1 | % Cells in S | % Cells in G2/M |
|---|---|---|---|
| DMSO (control) | 81.31 | 10.54 | 8.15 |
| 5.78 µM Compound 29 | 47.32 | 23.71 | 28.97 |

The invention claimed is:

1. A compound of formula (IIB)

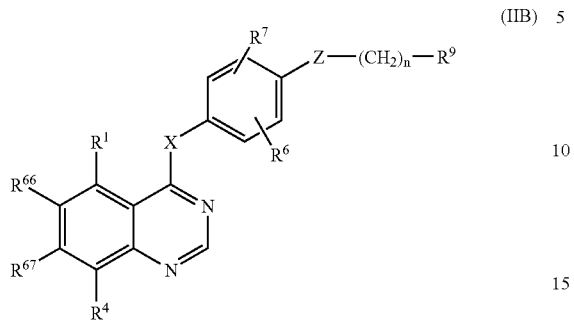

or a salt thereof where

X is O, or S, S(O) or S(O)$_2$, NH or NR$^8$ where R$^8$ is hydrogen or C$_{1-6}$alkyl, Z is O or S, n is an integer of from 1 to 6 and R$^9$ is hydrogen, or n is 0 or an integer of from 1 to 6 and R$^9$ is ethenyl, optionally substituted phenyl, optionally substituted pyridyl or optionally substituted furanyl where optional substituents for R$^9$ groups are C$_{1-3}$alkoxy, C$_{1-3}$alkyl, halo or nitro, R$^6$ and R$^7$ are independently selected from hydrogen, halo, C$_{1-4}$alkyl, C$_{1-4}$alkoxy, C$_{1-4}$alkoxymethyl, di(C$_{1-4}$alkoxy)methyl, C$_{1-4}$alkanoyl, trifluoromethyl, cyano, amino, C$_{2-5}$alkenyl, C$_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated and linked via a ring carbon or nitrogen atom or unsaturated and linked via a ring carbon atom, and which phenyl, benzyl or heterocyclic group may bear on one or more ring carbon atoms up to 5 substituents selected from hydroxy, halogeno, C$_{1-3}$alkyl, C$_{1-3}$alkoxy, C$_{1-3}$alkanoyloxy, trifluoromethyl, cyano, amino, nitro, C$_{2-4}$alkanoyl, C$_{1-4}$alkanoylamino, C$_{1-4}$alkoxycarbonyl, C$_{1-4}$alkylsulphanyl, C$_{1-4}$alkylsulphinyl, C$_{1-4}$alkylsulphonyl, carbamoyl, N—C$_{1-4}$alkylcarbamoyl, N,N-di(C$_{1-4}$alkyl)carbamoyl, aminosulphonyl, C$_{1-4}$alkylaminosulphonyl, N,N-di(C$_{1-4}$alkyl)aminosulphonyl, C$_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, C$_{1-3}$alkyl, C$_{1-3}$alkoxy, C$_{1-3}$alkanoyloxy, trifluoromethyl, cyano, amino, nitro and C$_{1-4}$alkoxycarbonyl, R$^1$ is hydrogen, R$^4$ is hydrogen, halo, C$_{1-4}$alkyl or C$_{1-4}$alkoxy, R$^{66}$ is halo, cyano, nitro, trifluoromethyl, C$_{1-3}$alkyl, —NR$^{12}$R$^{13}$, wherein R$^{12}$ and R$^{13}$, which may be the same or different, each represents hydrogen or C$_{1-3}$alkyl, or a group —X$^1$R$^{14}$ wherein X$^1$ represents a direct bond, —O—, —CH$_2$—, —OC(O)—, —C(O)—, —S—, —SO—, —SO$_2$—, —NR$^{15}$C(O)—, —C(O)NR$^{16}$—, —SO$_2$NR$^{17}$—, —NR$^{18}$SO$_2$— or —NR$^{19}$— wherein R$^{15}$, R$^{16}$, R$^{17}$, R$^{18}$ and R$^{19}$ each independently represents hydrogen, C$_{1-3}$alkyl or C$_{1-3}$alkoxy C$_{2-3}$alkyl, and R$^{14}$ is hydrogen or C$_{1-5}$alkyl which may be unsubstituted or which may be substituted with one or more groups selected from hydroxy, oxiranyl, fluoro, chloro, bromo and amino including C$_{1-3}$alkyl and trifluoromethyl; or —R$^9$R$^{38}$ and wherein R$^{38}$ represents a pyridone group, a phenyl group or a 5–6-membered aromatic heterocyclic group linked via carbon or nitrogen with 1–3 heteroatoms selected from O, N and S, which pyridone, phenyl or aromatic heterocyclic group may carry up to 5 substituents selected from hydroxy, nitro, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxy, carboxamido, trifluoromethyl, cyano, —C(O)NR$^{39}$R$^{40}$, —NR$^{41}$C(O)R$^{42}$ wherein R$^{39}$, R$^{40}$, R$^{41}$ and R$^{42}$, which may be the same or different, each represents hydrogen, C$_{1-4}$alkyl, hydroxyC$_{1-4}$alkyl or C$_{1-3}$alkoxyC$_{2-3}$alkyl and a group —(—O—)$_f$(C$_{1-4}$alkyl)$_g$ringD wherein f is 0 or 1, g is 0 or 1 and ring D is a cyclic group selected from C$_{3-6}$cycloalkyl, aryl or 5–6-membered saturated or unsaturated heterocyclic group with 1–2 heteroatoms, selected independently from O, S and N, which cyclic group may bear one or more substituents selected from halo and C$_{1-4}$alkyl; and wherein R$^9$ is a C$_{1-8}$alkylene group optionally substituted by one or more substituents selected from hydroxy, halogeno and amino;

and R$^{67}$ is C$_{1-6}$alkoxy substituted with a group X$^1$R$^{38}$ wherein X$^1$ and R$^{38}$ are as defined above or R$^{67}$ is 3-morpholinopropoxy.

2. A method of preparing a compound according to claim 1, which comprises reacting a compound of formula (VII)

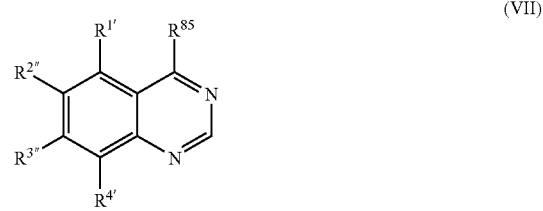

where R$^{1'}$, R$^{2''}$, R$^{3'''}$, and R$^{4'}$ are respectively equivalent to a group R$^1$, R$^{66}$, R$^{67}$ and R$^4$ as defined in claim 1 or a precursor thereof, and R$^{85}$ is a leaving group, with a compound of formula (VIII)

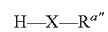 (VIII)

where X, is as defined in claim 1, and R$^{a''}$ is

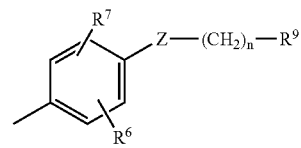

where Z, n, R$^6$, R$^7$ and R$^9$ are as defined in claim 1.

3. A pharmaceutical composition comprising a compound of formula (IIB) as defined in claim 1, or a salt thereof, in combination with a pharmaceutically acceptable carrier.

4. A compound according to claim 1 or a salt thereof wherein $R^1$ and $R^4$ are both hydrogen.

5. A compound according to claim 1 wherein $R^{67}$ is 3-morpholinopropoxy.

6. A compound according to claim 1 wherein $R^6$ and $R^7$ are independently selected from hydrogen, halo, $C_{1-4}$alkoxy, cyano, trifluoromethyl or phenyl.

7. A compound according to claim 1 wherein $R^6$ and $R^7$ are both hydrogen.

8. A method of treating colorectal or breast cancer in a warm blooded animal comprising administering to said animal an effective amount of a compound according to claim 1 or a salt thereof.

* * * * *